US008008271B2

(12) United States Patent
Xu et al.

(10) Patent No.: US 8,008,271 B2
(45) Date of Patent: Aug. 30, 2011

(54) METHODS AND COMPOSITIONS FOR TREATING GAIN-OF-FUNCTION DISORDERS USING RNA INTERFERENCE

(75) Inventors: Zuoshang Xu, Wellesley, MA (US); Xugang Xia, Westborough, MA (US)

(73) Assignee: University of Massachusetts, Boston, MA (US)

( * ) Notice: Subject to any disclaimer, the term of this patent is extended or adjusted under 35 U.S.C. 154(b) by 110 days.

(21) Appl. No.: 12/175,369

(22) Filed: Jul. 17, 2008

(65) Prior Publication Data

US 2009/0042828 A1    Feb. 12, 2009

Related U.S. Application Data

(63) Continuation of application No. 11/101,162, filed on Apr. 6, 2005, now Pat. No. 7,498,316.

(60) Provisional application No. 60/560,179, filed on Apr. 6, 2004.

(51) Int. Cl.
*A61K 31/70* (2006.01)
*C07H 21/04* (2006.01)

(52) U.S. Cl. ........................................ 514/44; 536/24.5

(58) Field of Classification Search ........................ None
See application file for complete search history.

(56) References Cited

U.S. PATENT DOCUMENTS

| | | | |
|---|---|---|---|
| 2003/0069195 | A1 | 4/2003 | Farrar et al. |
| 2003/0180756 | A1* | 9/2003 | Shi et al. ............................ 435/6 |
| 2003/0190635 | A1 | 10/2003 | McSwiggen |
| 2004/0023390 | A1 | 2/2004 | Davidson et al. |
| 2004/0192629 | A1 | 9/2004 | Xu et al. |
| 2004/0214198 | A1 | 10/2004 | Rana |
| 2004/0219671 | A1 | 11/2004 | McSwiggen et al. |
| 2004/0241854 | A1 | 12/2004 | Davidson et al. |
| 2005/0042646 | A1 | 2/2005 | Davidson et al. |
| 2005/0130184 | A1 | 6/2005 | Xu et al. |
| 2005/0130919 | A1 | 6/2005 | Xu et al. |
| 2005/0137155 | A1 | 6/2005 | McSwiggen et al. |

FOREIGN PATENT DOCUMENTS

| | | |
|---|---|---|
| WO | 03/070895 A2 | 8/2003 |
| WO | 03/080807 A2 | 10/2003 |
| WO | 2004/01335 A1 | 2/2004 |
| WO | 2004/013280 A2 | 2/2004 |
| WO | 2004/013310 A2 | 2/2004 |
| WO | 2004/042027 A2 | 5/2004 |
| WO | 2004/046324 A2 | 6/2004 |
| WO | 2004/058940 A2 | 7/2004 |
| WO | 2005/003350 A1 | 1/2005 |
| WO | 2005/007875 A2 | 1/2005 |
| WO | 2005/007877 A2 | 1/2005 |
| WO | 2005/023991 A2 | 3/2005 |
| WO | 2005/027980 A1 | 3/2005 |
| WO | 2005/045034 A2 | 7/2005 |

OTHER PUBLICATIONS

Kim et al. Antisense and Nucleic Acid Drug Development 2003, vol. 13, pp. 151-155.*
Bass, B.L., "RNA interference. The Short Answer," Nature, vol. 411(6836):428-429 (2001).
Ding, Hongliu et al., "Selective silencing by RNAi of a dominant allele that causes amyotrophic lateral sclerosis," Aging Cell, vol. 2:209-217 (2003).
Harper, Scott Q. et al., "RNA interference improves motor and neuropathological abnormalities in a Huntington's disease mouse model," PNAS, vol. 102(16):5820-5825 (2005).
Maxwell, Michele M. et al., "RNA interference-mediated silencing of mutant superoxide dismutase rescues cyclosporin A-induced death in cultured neuroblastoma cells," PNAS, vol. 101(9):3178-3183 (2004).
Miller et al. "Allele-specific silencing of dominant disease genes." PNAS, 100(12): 7195-7200 (2003).
Miller, Victor M. et al., "Targeting Alzheimer's disease genes with RNA interference: an efficient strategy for silencing mutant alleles," Nucleic Acids Research, vol. 32(2):661-668 (2004).
Ralph, G. Scott et al., "Silencing mutant SOD1 using RNAi protects against neurodegeneration and extends survival in an ALS model," Nature Medicine, vol. 11(4):429-433 (2005).
Raoul, Cedric et al., "Lentiviral-mediated silencing of SOD1 through RNA interference retards disease onset and progression in a mouse model of ALS," Nature Medicine, Vol. 11(4):423-428 (2005).
Rival, Thomas et al., "Decreasing Glutamate Buffering Capacity Triggers Oxidative Stress and Neuropil Degeneration in the Drosophila Brain," Current Biology, vol. 14:599-605 (2004).
Sui, Guangchao et al., "A DNA vector-based RNAi technology to suppress gene expression in mammalian cells," PNAS, vol. 99(8):5515-5520 (2002).
Veldink, Jan H. et al., "The future of motor neuron disease," J. Neurol., vol. 241:491-500 (2004).
Xia, Xu Gang et al., "An enhanced U6 promoter for synthesis of short hairpin RNA," Nucleic Acids Research, vol. 31 (17):e100 (2003).
Xia, Xu Gang et al., "An RNAi strategy for treatment of amyotrophic lateral sclerosis caused by mutant Cu,Zn superoxide dismutase," Journal of Neurochemistry, vol. 92:362-367 (2005).
Xie, Jun et al., "RNAi knockdown of Par-4 inhibits neurosynaptic degeneration in ALS-linked mice," Journal of Neurochemistry, vol. 92:59-71 (2005).
Xie, Zhongcong et al., "Effects of RNA Interference-mediated Silencing of g-Secretase Complex Components on Cell Sensitivity to Caspase-3 Activation," The Journal of Biological Chemistry, vol. 279(33):34130-34137 (2004).

* cited by examiner

*Primary Examiner* — Tracy Vivlemore
(74) *Attorney, Agent, or Firm* — Nelson Mullins Riley & Scarborough LLP; Debra J. Milasincic, Esq.

(57) ABSTRACT

The present invention relates to novel methods for treating dominant gain-of-function diseases. The invention provides methods for targeting regions of the copper zinc superoxide dismutase (SOD1), which causes inherited amyotrophic lateral sclerosis (ALS), with RNAi agent. The invention further provides RNAi resistant replacement genes containing mismatches with their respective RNAi agents. The invention also provides for vectors that express RNAi agent and RNAi resistant replacement gene of the present invention.

14 Claims, 5 Drawing Sheets

Fig. 2
A
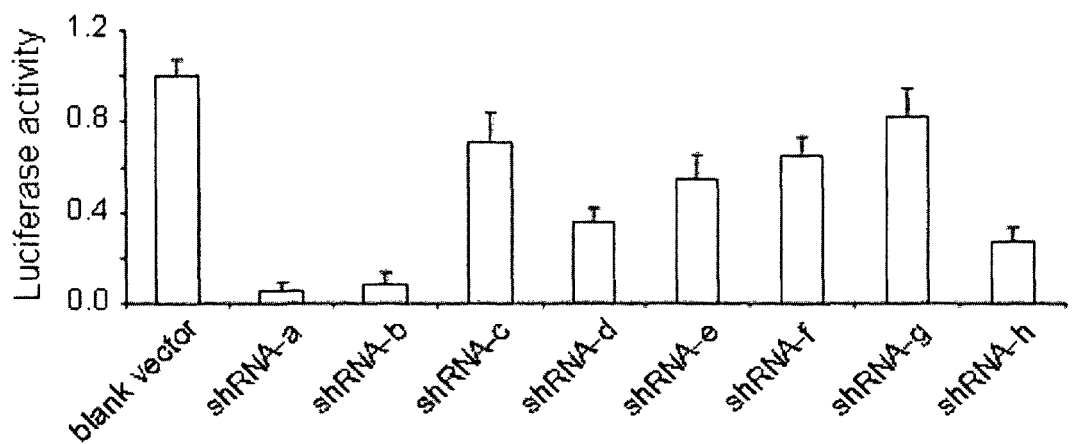
B
```
SOD1a    AUG...GGGCAACGUAACGGCUGACAAAGAUGGUGUGGCCGAUGUGUCUAUUGAAGAUUC...UAA
                   ||||  ||  ||  ||||||||||||
ShRNAa             CGUUACACUGACGACUGUUUC-5'
                   ||||||||||||||||||||||
SOD1     AUG...GGGCAAUGUGACUGCUGACAAAGAUGGUGUGGCCGAUGUGUCUAUUGAAGAUUC...UAA
                                        |||||||||||||||||||||
ShRNAb                                  CGGCUACACAGAUAACUUCUA-5'
                                        |||||  |||   |||||||||
SOD1b    AUG...GGGCAAUGUGACUGCUGACAAAGAUGGUGUGGCCGACGUGAGUAUUGAAGAUUC...UAA
```
C
Endogenous SOD1

Fig. 3

Hairpin-one: hSOD1hp-1, located at 256-277 from start codon

SEQ ID NO:1  5-GGCAATGTGACTGCTGACAAAG-3    22bp
SEQ ID NO:2  3-CCGTTACACTGACGACTGTTTC-5

First replacement human SOD1: hSOD1-1

SEQ ID NO:3  5-GGAAACGTCACGGCGGATAAAG-3    hSOD1-1 target sense
SEQ ID NO:4  3-CCGUUACAGUGACGACUGUUUC-5   shRNA antisense 22bp

Hairpin-three: hSOD1hp-3, located at 286-307 from start codon

SEQ ID NO:5  5-GCCGATGTGTCTATTGAAGAT-3    21bp
SEQ ID NO:6  3-CGGCTACACAGATAACTTCTA-5

Second replacement human SOD1: hSOD1-3

SEQ ID NO:8  5-GCAGACGTCAGTATAGAGGAC-3    hSOD1-3 target sense
SEQ ID NO:7  3-CGGCUACACAGAUAACUUCUA-5   shRNA antisense 21bp

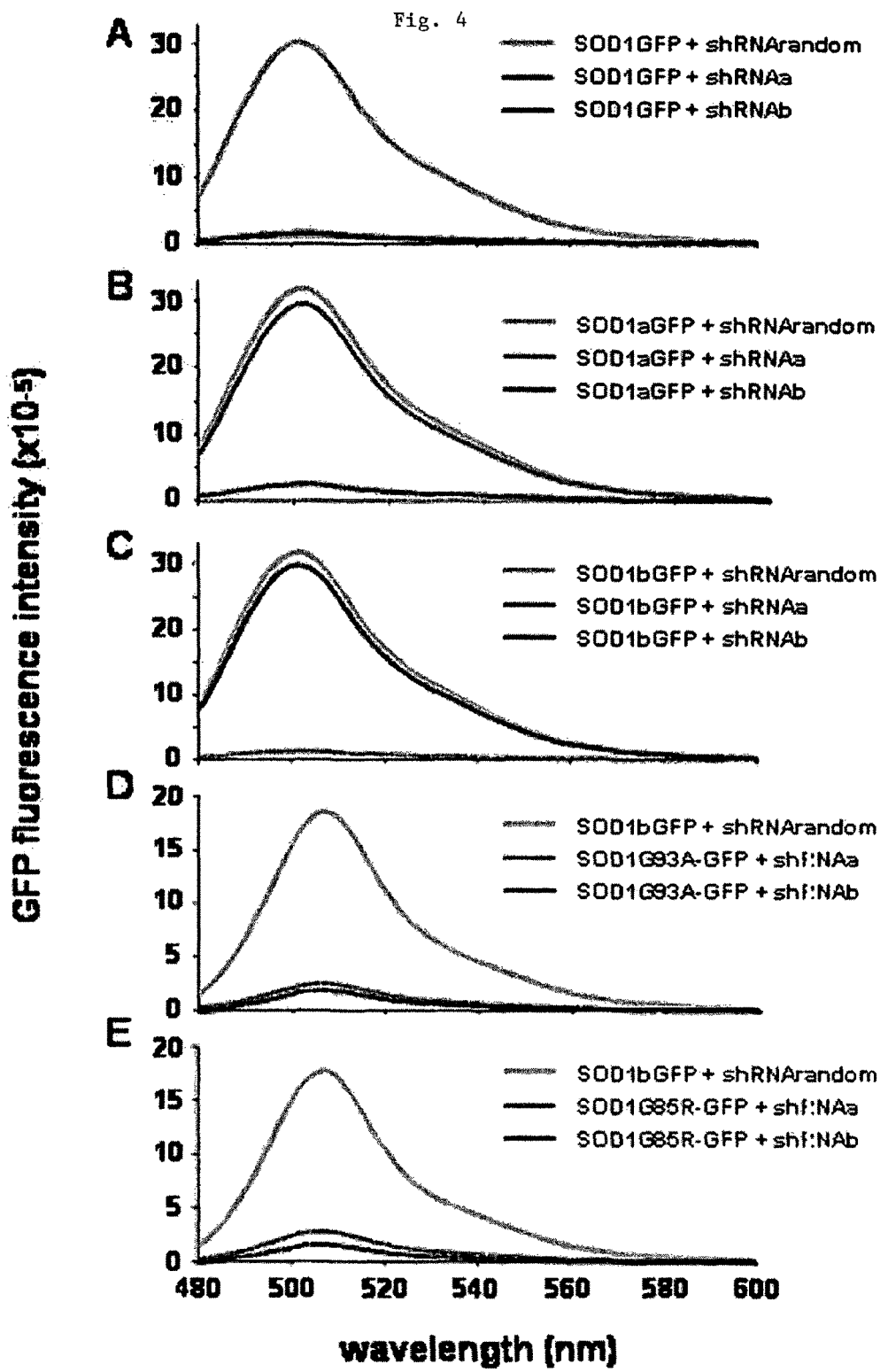

METHODS AND COMPOSITIONS FOR TREATING GAIN-OF-FUNCTION DISORDERS USING RNA INTERFERENCE

RELATED APPLICATIONS

This patent application claims the benefit of U.S. patent application Ser. No. 11/101,162, entitled "Methods and Compositions for Treating Gain-Of-Function Disorders Using RNA Interference", filed Apr. 6, 2005 which claims the benefit of U.S. Provisional Patent Application Ser. No. 60/560,179, entitled "General Strategy for Treating Mutant SOD 1-induced ALS using RNAi", filed Apr. 6, 2004. The entire contents of the above-referenced applications are incorporated herein by this reference.

GOVERNMENT RIGHTS

This invention was made with government support under Grant no. NS041739 awarded by the National Institutes of Health, and Grant no: 5-26076 awarded by the National Institute of Neurological Disorders and Stroke (NINDS). The government has certain rights in the invention.

BACKGROUND OF THE INVENTION

Diseases caused by dominant, gain-of-function gene mutations develop in heterozygotes bearing one mutant and one wild type copy of the gene. Some of the best-known diseases of this class are common neurodegenerative diseases, including Alzheimer's disease, Huntington's disease, Parkinson's disease and amyotrophic lateral sclerosis (ALS; "Lou Gehrig's disease") (Taylor et al., 2002). In these diseases, the exact pathways whereby the mutant proteins cause cell degeneration are not clear, but the origin of the cellular toxicity is known to be the mutant protein.

Mutations in SOD1 cause motor neuron degeneration that leads to ALS, because the mutant protein has acquired some toxic property (Cleveland et al., 2001). Neither the nature of this toxic property nor the downstream pathway that leads to the eventual motor neuron degeneration is understood. In mice, only expression of the mutant SOD1, but not elimination of SOD1 by gene knockout, causes ALS. Nonetheless, the gene knockout mice develop numerous abnormalities including reduced fertility (Matzuk et al., 1990), motor axonopathy (Shefner et al., 1999), age-associated loss of cochlear hair cells (McFadden et al., 2001) and neuromuscular junction synapses (Flood et al., 1999), and enhanced susceptibility to a variety of noxious assaults, such as excitotoxicity, ischemia, neurotoxins and irradiation, on the CNS and other systems (Matz et al., 2000; Kondo et al., 1997; Kawase et al., 1999; Behndig et al., 2001).

More than 100 mutations in SOD1 cause ALS. The severity of the disease is correlated with accumulation of mutant protein. Previous research has demonstrated that the level of mutant SOD 1 can be specifically lowered using RNAi targeting the mutation sites. The selective inhibition of mutant SOD1 but not wild-type SOD1 expression avoids the adverse effects resulting from inhibition of the wild type SOD1 expression. Treatment of ALS patients with SOD1 mutations by targeting each mutation site may have certain complexities. For example, a large number of vectors may be needed to target each mutant. In addition, mutation sites may vary in terms of RNAi efficiency and specificity. Improved therapies for treating this disease, as well as other gain-of-function diseases, efficiently and selectively block the expression of the mutant protein while retaining expression of the wild type.

SUMMARY

The present invention relates to methods and reagents for treating a variety of gain-of-function diseases. In one aspect, the invention relates to methods and reagents for treating a variety of diseases characterized by a mutation in one allele or copy of a gene, the mutation encoding a protein which is sufficient to contribute to or cause the disease. Preferably, the methods and reagents are used to treat diseases caused or characterized by a mutation that is inherited in an autosomal dominant fashion.

The present invention utilizes RNA interference technology against a target sequence located within a gene encoding a gain-of-function mutant protein, e.g. a mutant huntingtin protein or a mutant SOD1 protein. RNAi agents of the present invention silence the expression of the corresponding mutant mRNA with sequence specificity and selectivity. However, these RNAi agents do not target the mutation site which is unique to the gain-of-function mutant gene. The RNAi agents comprise first and second strands each containing 16-25 nucleotides. The first strand of the present invention is homologous to a region of a gene that does not contain the mutation site. The second strand includes 16-25 nucleotides complementary to the first strand. Accordingly, the RNAi agents of the invention do not discriminate between the gain-of-function mutant and wild-type, and therefore, inhibit expression of both wild-type and gain-of-function mutant alleles of a target gene.

To compensate for the loss of wild-type expression, the invention further provides RNAi resistant replacement genes. These RNAi resistant replacement genes contain mismatches with their respective RNA silencing agents and are resistant to the RNA silencing induced by their respective RNA silencing agents.

In particular embodiments, the invention provides methods and compositions for targeting regions in the human copper zinc superoxide dismutase SOD1 mRNA with RNAi agents, e.g., siRNAs and small hairpin RNAs (shRNAs) e.g., hSOD1hp-1 and hSOD1hp-2. These RNAi agents (e.g., siRNAs and shRNAs) do not discriminate between the mutant and wild-type SOD1, and therefore, inhibit both the mutant and wild-type SOD1 expression. To compensate for the loss of wild-type SOD1 expression, the invention further provides RNAi resistant replacement genes e.g., hSOD1-1 and hSOD1-2. These RNAi resistant replacement genes contain mismatches with their respective shRNAs and are resistant to the RNAi induced by their respective shRNAs. In addition, the present invention further provides a vector that produces an shRNA that inhibits endogenous SOD1 expression, including both the mutant and the wild-type, but at the same time, expresses the RNAi resistant replacement genes that are resistant to shRNA-induced silencing In exemplary embodiments, the siRNA sense strand comprises about 16 to 22 nucleotides and the corresponding antisense strand comprises about 16 to 22 nucleotides the strands optionally aligned such that the ends for 2-3 nucleotide overhangs. In one embodiment, the siRNA sense strand comprises SEQ ID NO:1, and the corresponding antisense strand comprises SEQ ID NO:2. In another embodiment, the siRNA sense strand comprises SEQ ID NO:5, and its corresponding antisense strand comprises SEQ ID NO:6.

In another aspect, the invention provides for an RNAi-resistant replacement gene which encodes SOD1. In preferred embodiments, the RNAi-resistant replacement gene contains a silent mutation e.g., a mutation as compared to the wild-type gene sequence having no functional consequence in the encoded protein. In one embodiment, the RNAi-resistant replacement gene comprises SEQ ID NO:3 or SEQ ID NO: 8. In yet another embodiment, the silent mutation is selected from the group consisting of an adenine at position 3; a cytosine at position 5 and 8; a guanine at position 11 and 14; and a thymine at position 17 of SEQ ID NO:3. In yet a further embodiment, the silent mutation is selected from the group consisting of an adenine at position 3, 10 and 15; a cytosine at position 6, 9 and 21; and a guanine at position 11 and 18 of SEQ ID NO:8.

In another embodiment, the invention provides an expression construct comprising an isolated nucleic acid that encodes one or more nucleic acid molecules, e.g. a RNAi agent and/or RNAi resistant replacement gene, of the invention. The expression construct can be for example, a viral vector (e.g., an adeno-associated virus (AAV) or lentiviral vector), expression cassette or plasmid. In one embodiment, the invention features an expression construct (e.g., a vector, plasmid, cassette etc.) comprising a first polynucleotide sequence encoding an RNAi agent (e.g., an siRNA precursor, specific for a target gene e.g., hSOD1hp-1, hSOD1hp-2 and hSOD1hp-3, and a second polynucleotide sequence corresponding to a RNAi resistant replacement gene. In one embodiment, the RNAi agent is a hairpin RNA or precursor RNA. The hairpin RNA is designed such that it is cleaved by the enzyme Dicer of a cell into a duplex RNA capable of mediating RNAi (e.g., an siRNA). In one embodiment, the siRNA comprises a sense RNA strand and an antisense RNA strand, the antisense strand having a sequence sufficiently complementary to a target RNA to direct cleavage via RNAi. The antisense strand sequence, however, lacks sufficient complementarity to direct RNAi against the RNAi-resistant replacement gene. In preferred embodiments, the RNAi-resistant replacement gene is expressed in the presence of the RNAi agent.

In another aspect, the invention provides a vector encoding the siRNA and RNAi-resistant replacement gene. In certain embodiments, the vector is a conditional expression vector. In another embodiment, the invention provides a host cell containing a vector of the invention. In yet another embodiment, the invention provides for a kit which includes the reagents for activating target-specific RNA interference (RNAi) in a cell or organism e.g., a vector encoding the siRNA and including RNAi-resistant replacement gene optionally packaged with instructions for use with a suitable control.

In another aspect, the invention provides method of inhibiting expression of a gain-of-function mutant gene and providing for expression of a replacement gene in a cell comprising administering to the cell a vector encoding a siRNA targeted to the mutant gene and including a RNAi-resistant replacement gene, whereby expression of the mutant gene is inhibited and expression of the RNAi-resistant replacement gene is achieved.

In another aspect, the invention provides therapeutic compositions comprising the vectors encoding the siRNAs and/or RNAi resistant replacement genes of the invention, and a pharmaceutically acceptable carrier.

In another aspect, the present invention provides a method of treating a subject having or at risk of having a disease (e.g. ALS) characterized or caused by a gain of function mutant protein (e.g. SOD1) by administering to the subject an effective amount of an RNA silencing targeting a sequence encoding the mutant protein, together with a RNA silencing resistant sequence, such that sequence-specific silencing of a gene occurs resulting in an effective treatment for the disease.

Other features and advantages of the invention will be apparent from the following detailed description, and from the claims.

BRIEF DESCRIPTION OF THE DRAWINGS

FIG. 2: Screening assay for selecting efficacious shRNAs against human SOD1. (A) A blank vector and eight shRNA vectors were cotransfected with Luc-SOD1 intro HEK293 cells. The silencing efficacy by each of the shRNAs was measured by the dual luciferase assay. The luciferase activity measures ratio of firefly luciferase activity to renilla luciferase activity, which was normalized to the average ration from the cells transfected with the blank shRNA vector. (B) The antisense stem sequence in the two most potent shRNAs: shRNA-a (SEQ ID NO: 75) and shRNA-b (SEQ ID NO: 7). The target mRNA region of human SOD1 (SEQ ID NO: 88) and the modified mRNA sequences encoded by the two replacement genes, SOD1a (SEQ ID NO: 87) and SOD1b (SEQ ID NO: 89), are also shown. (c) Western blot photograph showing that shRNA-a (lane-3) and shRNA-b (lane 4) inhibit the endogenous SOD1 gene expression in HEK293 cells. Lanes 1 and 2 are untransfected and blank vector transfected cells respectively.

FIG. 3: Two hairpins (hSOD1hp-1 and hSOD1hp-3) are designed to target two regions of the human SOD1 mRNA (SEQ ID NOs 1, 2 and 5, 6, respectively). Two RNAi resistant replacement genes (hSOD1-1 and hSOD1-3; SEQ ID NOs: 3, 4 and 7, 8, respectively) are designed to contain silent mutations in the respective target regions of the two SOD1 hairpins. The mismatched nucleotides between the RNAi resistant replacement genes and the anti-sense strand of the shRNA are boxed.

FIG. 4: Graphs depicting the results of a GFP reporter fluorescence assay. Hairpins targeting two SOD1-GFP mRNA regions, shRNA-a and shRNA-b, inhibited the expression of wild-type SOD1:GFP (FIG. 4A) and SOD1: GFP mutants G93A (FIG. 4D) and G85R (FIG. 4E). However, shRNA-a and shRNA-b did not inhibit the expression of the respective SOD1 RNAi-resistant replacement genes SOD1a:GFP (FIG. 4B) and SOD1b:GFP (FIG. 4C) containing silent codon changes in the target region.

DETAILED DESCRIPTION OF THE INVENTION

Figure 1:
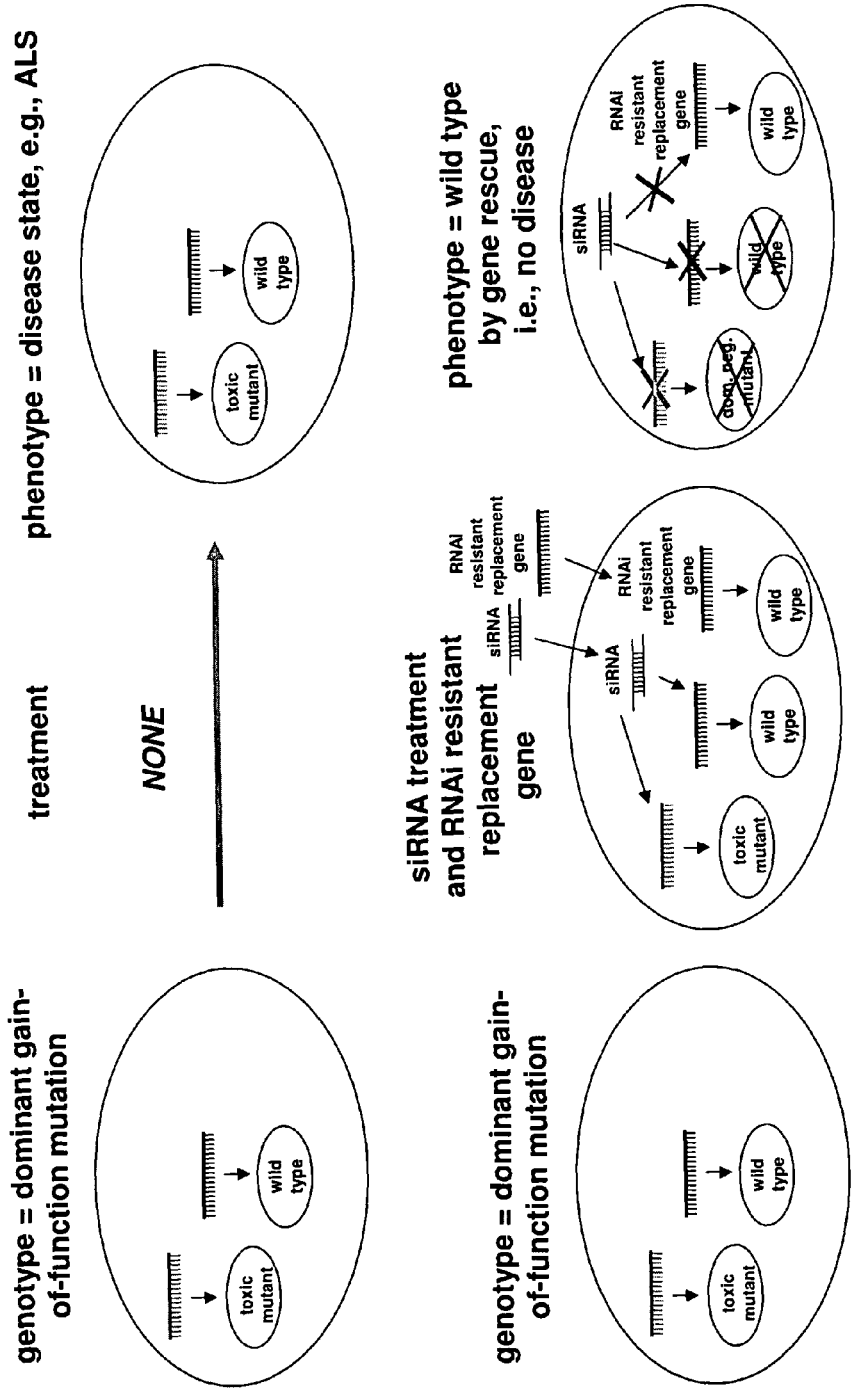
FIG. 1: A schematic diagram depicting SOD1 targeting and wild-type SOD1 gene rescue utilizing siRNAs targeting the human SOD1 mRNA and an RNAi resistant replacement gene.

Mutations in copper zinc superoxide dismutase (SOD1) gene cause a subset of amyotrophic lateral sclerosis, a neurodegenerative disease that leads to motor neuron degeneration, paralysis and death (Brown and Robberecht, 2001; Siddique and Lalani, 2002). It has been well established that mutant SOD1 causes motor neuron degeneration by acquisition of a toxic property (Cleveland and Rothstein, 2001). However, neither the molecular basis of this toxic property nor mechanism that leads to motor neuron death is understood. Because of this incomplete understanding of the disease mechanism, rational design of therapy has not produced robust efficacious outcomes. On the other hand, because the toxicity that kills motor neurons originates from the mutated protein (Cleveland and Rothstein, 2001), decrease of the mutant protein should alleviate or even prevent the disease. RNA interference (RNAi) technology can be used to achieve this goal.

The present invention features methods for targeting regions in the human copper zinc superoxide dismutase SOD1 mRNA with small hairpin RNAs (shRNAs) e.g., hSOD1hp-1 and hSOD1hp-2. These shRNAs do not discriminate between the mutant and wild-type SOD 1, and therefore, inhibit both the mutant and wild-type SOD1 expression. To compensate for the loss of wild-type SOD1 expression, the invention further provides resistant replacement genes e.g., hSOD1-1 and hSOD1-2. These RNAi resistant replacement genes contain mismatches with their respective shRNAs and are resistant to the RNAi induced by their respective shRNAs. In addition, the present invention further provides vectors that produce an shRNA that inhibits the endogenous SOD1 expression, including both the mutant and the wild-type, but at the same time, expresses the RNAi resistant replacement genes that are resistant to shRNA-induced silencing.

So that the invention may be more readily understood, certain terms are first defined:

The term "RNAi agent" as used herein means a composition that mediates sequence-specific RNA interference. The term "RNAi agent" includes both shRNAs, or precursor RNAs that are processed by RISC into siRNAs, as well as the siRNAs themselves that inhibits the expression of an endogenous gene, including both the mutant and the wild-type.

The term "RNAi resistant replacement gene" as used herein means a nucleotide sequence which encodes wild-type protein (e.g., SOD1) but which includes a silent mutation which makes the gene resistant to cleavage by a co-expressed RNAi agent.

An "isolated nucleic acid molecule or sequence" is a nucleic acid molecule or sequence that is not immediately contiguous with both of the coding sequences with which it is immediately contiguous (one on the 5' end and one on the 3' end) in the naturally occurring genome of the organism from which it is derived. The term therefore includes, for example, a recombinant DNA or RNA that is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide sequence.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, $^2$N-methylguanosine and $^{2,2}$N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

The term "engineered," as in an engineered nucleic acid molecule or precursor, indicates that the molecule is not found in nature, in that all or a portion of the nucleic acid sequence of the molecule is created or selected by man. Once created or selected, the sequence can be replicated, translated, transcribed, or otherwise processed by mechanisms within a cell.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising ~21 nucleotides (or nucleotide analogs), for example, 19, 20, 21 or 22 nucleotides. The term "long" siRNA refers to a siRNA comprising ~24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

As used herein, the term "antisense strand" of an siRNA or RNAi agent e.g., an antisense strand of an siRNA duplex or siRNA sequence, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific RNA interference (RNAi), e.g., complementarity sufficient to trigger the destruction of the desired target mRNA by the RNAi machinery or process. The term "sense strand" or "second strand" of an siRNA or RNAi agent e.g., an antisense strand of an siRNA duplex or siRNA sequence, refers to a strand that is complementary to the antisense strand or first strand. Antisense and sense strands can also be referred to as first or second strands, the first or second strand having complementarity to the target sequence and the respective second or first strand having complementarity to said first or second strand.

As used herein, the term "guide strand" refers to a strand of an RNAi agent, e.g., an antisense strand of an siRNA duplex or siRNA sequence, that enters into the RISC complex and directs cleavage of the target mRNA.

As used herein, the "5'end", as in the 5' end of an antisense strand, refers to the 5' terminal nucleotides, e.g., between one and about 5 nucleotides at the 5' terminus of the antisense strand. As used herein, the "3'end", as in the 3' end of a sense strand, refers to the region, e.g., a region of between one and about 5 nucleotides, that is complementary to the nucleotides of the 5' end of the complementary antisense strand The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2):77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference ("RNAi")" refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

An RNAi agent having a strand which is "sequence sufficiently complementary to a target mRNA sequence to direct target-specific RNA interference (RNAi)" means that the strand has a sequence sufficient to trigger the destruction of the target mRNA by the RNAi machinery or process.

The term "gene silencing" refers to the suppression of gene expression, e.g., transgene, heterologous gene and/or endogenous gene expression. Gene silencing may be mediated through processes that affect transcription and/or through processes that affect post-transcriptional mechanisms. In some embodiments, gene silencing occurs when siRNA initiates the degradation of the mRNA of a gene of interest in a sequence-specific manner via RNA interference (for a review, see Branti, 2002).

As used herein, the term "isolated RNA" (e.g., "isolated siRNA" or "isolated siRNA precursor") refers to RNA molecules which are substantially free of other cellular material, or culture medium when produced by recombinant techniques, or substantially free of chemical precursors or other chemicals when chemically synthesized.

A "target gene" is a gene whose expression is to be selectively inhibited or "silenced."

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. One portion or segment of a duplex stem of the shRNA structure is anti-sense strand or complementary, e.g., fully complementary, to a section of about 18 to about 40 or more nucleotides of the mRNA of the target gene.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder.

"Allele specific inhibition of expression" refers to the ability to significantly inhibit expression of one allele of a gene over another, e.g., when both alleles are present in the same cell. For example, the alleles can differ by one, two, three or more nucleotides. In some cases, one allele is associated with disease causation, e.g., a disease correlated to a dominant gain-of-function mutation.

The term "wild-type" refers to a gene or a gene product that has the characteristics of that gene or gene product when isolated from a naturally occurring source. A wild-type gene or gene product is that which is most frequently observed in a population and is thus arbitrarily designated the "normal" or "wild-type" form of the gene or gene product. In contrast, the term "mutant," as used herein, refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "mismatch" refers to a base pair consisting of noncomplementary bases, for example, not normal complementary G:C, A:T or A:U base pairs.

The term "transfecting" defines a number of methods to insert a nucleic acid vector or other nucleic acid molecules into a cellular organism. These methods involve a variety of techniques, such as treating the cells with high concentrations of salt, an electric field, detergent, or DMSO to render the outer membrane or wall of the cells permeable to nucleic acid molecules of interest or use of various viral transduction strategies.

The phrase "examining the function of a gene in a cell or organism" refers to examining or studying the expression, activity, function or phenotype arising there from.

As used herein, the term "kit" is used in reference to a combination of reagents and other materials which facilitates an assay and the analysis of a sample. In some embodiments, the kits of the present invention include a vector encoding a shRNA and an RNAi resistant replacement gene, optionally packaged with a suitable control or instructions for use.

As used herein, the term "subject" refers to any animal being examined, studied or treated. It is not intended that the present invention be limited to any particular type of subject. It is contemplated that multiple organisms will find use in the present invention as subjects. In some embodiments, humans are the preferred subject.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNAi agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Various aspects of the invention are described in further detail in the following subsections.

I. Gain-of-Function Disorders

Gain-of-function disorders are a class of disease or disorders characterized by a gain-of-function mutation. The term "gain-of-function mutation" as used herein, refers to any mutation in a gene in which the protein encoded by said gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein. In yet another embodiment, the disease or disorders of the present invention include neurodegenerative disease caused by a gain-of-function mutation. For example, Amyotrophic Lateral Sclerosis, Alzheimer's disease, Huntington's disease, and Parkinson's disease are associated with gain-of-function mutations in the genes encoding SOD1, Amyloid Precursor Protein or APP (see Ikezu et al, *EMBO J.*, (1996), 15(10):2468-75), Huntingtin or htt (see Rubinsztein, *Trends Genet.*, (2002), 18(4):202-9), and alpha-synuclein (see, for example, Cuervo et al., *Science*, (2004), 305(5688): 1292-5), respectively. In another embodiment, disease or disorders of the present invention include neurodegenerative disease caused by a gain-of-function mutation in an oncogene, e.g., cancers caused by a mutation in the ret oncogene (e.g., ret-1), for example, gastrointestinal cancers, endocrine tumors, medullary thyroid tumors, parathyroid hormone tumors, multiple endocrine neoplasia type2, and the like. In a more preferred embodiment, the disease or disorder of the present invention is Amyotrophic Lateral Sclerosis.

A. Amyotrophic Lateral Sclerosis (ALS)

Amyotrophic lateral sclerosis (ALS), also known as Lou Gehrig's disease, is a progressive, fatal neurodegenerative disorder involving the motor neurons of the cortex, brain stem, and spinal cord (Hirano, A., 1996, Neurology 47 (Suppl. 2), S63-S66). The disease is caused by a dominant, gain-of-function mutation that develops in people bearing one mutant and one wild type copy of the gene e.g., SOD1. ALS causing SOD1 mutations are single-nucleotide point mutations that alter a single amino acid in the protein. The disease is further characterized by a progressive motor neuron degeneration leading to paralysis, to total loss of motor and respiratory functions, and eventually to death in two to eight years after the appearance of the first clinical signs (mean duration after onset three years). ALS is of genetic origin in 10% of the patients, and sporadic in 90% of the cases. Point mutations in the gene encoding for copper zinc superoxide dismutase (SOD1) localized on chromosome 21q22-1 are responsible for the pathology in 20% of the familial cases (Rosen et al., Mutations in Cu/Zn superoxide dismutase gene are associated with familial amyotrophic lateral sclerosis, Nature, 362, 59-62, 1993, review in Rowland, Amyotrophic lateral sclerosis: Human challenge for neuroscience, Proc. Natl. Acad. Sci. USA, 92, 1251-1253, 1995). Thus, defective SOD1 is linked to motor neuron death and carries implications for understanding and possible treatment of familial amyotrophic lateral sclerosis.

i. The SOD-1 Gene

SOD1 is a metalloenzyme that contains one copper and one zinc, and is present in the cytoplasm as a homodimer. Copper is required for enzymatic activity while zinc stabilizes the protein's structure (Fridovich, 1986). SOD1 is a expressed in all eukaryotic cells and is one of a family of three SOD enzymes, including manganese-dependent, mitochondrial SOD (SOD2) and copper/zinc extracellular SOD (SOD3) (I Fridovich, 1986, "Superoxide dismutases," Advances in Enzymology 58: 61-97). The main natural function of SOD1 is superoxide dismutation, in which superoxide ($O_2^-$) is converted to hydrogen peroxide ($H_2O_2$) and oxygen. Together with the downstream enzymes catalase and glutathione peroxidase (which convert $H_2O_2$ to water and oxygen), SOD1 detoxifies cellular free radicals. The importance of this function is underscored by numerous abnormalities in mice lacking the SOD1 gene, including reduced fertility (Matzuk et al., 1998), motor axonopathy (Shefner et al., 1999), increased age-associated loss of cochlear hair cells (McFadden et al., 2001) and neuromuscular junction synapses (Flood et al., 1999), and enhanced susceptibility to a variety of noxious assaults on the nervous system, such as axonal injury (Reaume et al., 1996), ischemia (Kondo et al., 1997; Kawase et al., 1999), hemolysate exposure (Matz et al., 2000) and irradiation (Behndig et al., 2001). Given the toxicity of the mutant, an ideal therapy for treating this disease would be to selectively block the expression of the mutant protein while retaining expression of the wild type protein.

ii. SOD-1 Mutant Gene

More than 100 SOD1 mutations have been identified. Most of these mutations produce a single amino acid replacement in the superoxide dismutase enzyme's chain of amino acids. The most common substitution, which occurs in 50 percent of American patients with type 1 amyotrophic lateral sclerosis, is the replacement of alanine with valine at position 4 in the amino acid chain (also written as Ala4Val).

SOD1 mutations affect the age when symptoms of type 1 amyotrophic lateral sclerosis begin and how fast the disease progresses. The Ala4Val mutation, for example, results in an aggressive form of the disorder with a survival time of less than 2 years after disease onset. The replacement of glycine with arginine at position 37 (Gly37Arg) is associated with early onset of the disease but a longer survival time. In addition, other factors in combination with SOD1 mutations probably vary the course of type 1 amyotrophic lateral sclerosis. For example, mutations in both the SOD1 gene and a gene known as CNTF appear to accelerate the onset of the disease. The CNTF mutation alone has no ill effects, but in combination with the SOD1 mutation, disease symptoms appear decades earlier compared to other affected family members.

It remains unclear how SOD1 mutations lead to the selective death of motor neurons, which are the specialized nerve cells in the brain and spinal cord that control muscle movement. The superoxide dismutase enzyme is thought to gain a new (but still undefined) toxic function as a result of changes in the SOD1 gene. The malfunctioning enzyme may cause the death of motor neurons through an accumulation of harmful superoxide radicals, abnormal production of other types of toxic radicals, promotion of cell suicide (apoptosis), clumping of the enzyme with other cell proteins, or continued stimulation of motor neurons that cause them to burn out and die (excitotoxicity).

The wild type SOD1 sequence and several known SOD1 mutations are set forth in Tables 1 and 2, respectively:

TABLE 1

Homo sapiens superoxide dismutase 1, soluble (amyotrophic lateral sclerosis 1 (adult)) (SOD1), cDNA (SEQ ID NO: 74)

```
  1 ctgcagcgtc tggggtttcc gttgcagtcc tcggaaccag gacctcggcg tggcctagcg 61 agttatggcg acgaaggccg tgtgcgtgct gaagggcgac ggcccagtgc agggcatcat 121 caatttcgag cagaaggaaa gtaatggacc agtgaaggtg tggggaagca ttaaaggact 181 gactgaaggc ctgcatggat tccatgttca tgagtttgga gataatacag caggctgtac 241 cagtgcaggt cctcacttta atcctctatc cagaaaacac ggtgggccaa aggatgaaga 301 gaggcatgtt ggagacttgg gcaatgtgac tgctgacaaa gatggtgtgg ccgatgtgtc 361 tattgaagat tctgtgatct cactctcagg agaccattgc atcattggcc gcacactggt 421 ggtccatgaa aaagcagatg acttgggcaa aggtggaaat gaagaaagta caaagacagg 481 aaacgctgga agtcgtttgg cttgtggtgt aattgggatc gcccaataaa cattcccttg 541 gatgtagtct gaggccccct aactcatctg ttatcctgct agctgtagaa atgtatcctg 601 ataaacatta aacactgtaa tcttaaaagt gtaattgtgt gacttttca gagttgcttt 661 aaagtacctg tagtgagaaa ctgatttatg atcacttgga agatttgtat agttttataa 721 aactcagtta aaatgtctgt ttcaatgacc tgtattttgc cagacttaaa tcacagatgg
```

TABLE 1-continued

Homo sapiens superoxide dismutase 1, soluble (amyotrophic lateral sclerosis 1 (adult)) (SOD1), cDNA (SEQ ID NO: 74)

```
781 gtattaaact tgtcagaatt tctttgtcat tcaagcctgt gaataaaaac cctgtatggc 841 acttattatg aggctattaa aagaatccaa attc
```

(the skilled artisan will appreciate that the SOD1 mRNA sequence is the same as the cDNA sequence depicted above, but for the presence of uracil (U) in the place of thymine (T))

TABLE 2

Known SOD1 mutations

| Location | nt | aa | | | |
|---|---|---|---|---|---|
| exon 1 | 93 | 4 | Ala4Ser | Ala4Thr | Ala4Val |
| exon 1 | 99 | 6 | Cys6Gly | Cys6Phe | |
| exon 1 | 103 | 7 | Val7Glu | | |
| exon 1 | 105 | 8 | Leu8Val | Leu8Gln | |
| exon 1 | 112 | 10 | Gly10Val | Gly10Gly | |
| exon 1 | 117 | 12 | Gly12Arg | | |
| exon 1 | 123 | 14 | Val14Met | Val14Gly | |
| exon 1 | 129 | 16 | Gly16Ser | Gly16Ala | |
| exon 1 | 142 | 20 | Phe20Cys | | |
| exon 1 | 144 | 21 | Glu21Lys | Glu21Gly | |
| exon 1 | 148 | 22 | Gln22Leu | | |
| intron 1 | 319 | | 319t > a | | |
| exon 2 | 466 | 37 | Gly37Arg | | |
| exon 2 | 469 | 38 | Leu38Val | Leu38Arg | |
| exon 2 | 478 | 41 | Gly41Ser | Gly41Asp | |
| exon 2 | 485 | 43 | His43Arg | | |
| exon 2 | 491 | 45 | Phe45Cys | | |
| exon 2 | 494 | 46 | His46Arg | | |
| exon 2 | 496 | 47 | Val47Phe | | |
| exon 2 | 500 | 48 | His48Arg | His48Gln | |
| exon 2 | 502 | 49 | Glu49Lys | | |
| exon 2 | 518 | 54 | Thr54Arg | | |
| exon 3 | 645 | 59 | Ser59Ile | Ser59Ser | |
| exon 3 | 663 | 65 | Asn65Ser | | |
| exon 3 | 669 | 67 | Leu67Arg | | |
| exon 3 | 683 | 72 | Gly72Cys | Gly72Ser | |
| exon 3 | 695 | 76 | Asp76Tyr | Asp76Val | |
| exon 4 | 1048 | 80 | His80Arg | | |
| exon 4 | 1059 | 84 | Leu84Val | Leu84Phe | |
| exon 4 | 1062 | 85 | Gly85Arg | | |
| exon 4 | 1066 | 86 | Asn86Ser | | |
| exon 4 | 1068 | 87 | Val87Met | Val87Ala | |
| exon 4 | 1071 | 88 | Thr88delACTGCTGAC | | |
| exon 4 | 1074 | 89 | Ala89Thr | Ala89Val | |
| exon 4 | 1078 | 90 | Asp90Ala | Asp90Val | |
| exon 4 | 1086 | 93 | Gly93Cys | Gly93Arg | Gly93Ser |
| | | | Gly93Asp | Gly93Ala | Gly93Val |
| exon 4 | 1092 | 95 | Ala95Thr | | |
| exon 4 | 1095 | 96 | Asp96Asn | | |
| exon 4 | 1098 | 97 | Val97Met | | |
| exon 4 | 1107 | 100 | Glu100Lys | Glu100Gly | |
| exon 4 | 1110 | 101 | Asp101Asn | Asp101Gly | |
| exon 4 | 1119 | 104 | Ile104Phe | | |
| exon 4 | 1122 | 105 | Ser105delTCACTC | Ser105Leu | |
| exon 4 | 1125 | 106 | Leu106Val | | |
| exon 4 | 1132 | 108 | Gly108Val | | |
| exon 4 | 1144 | 112 | Ile112Thr | Ile112Met | |
| exon 4 | 1146 | 113 | Ile113Phe | Ile113Thr | |
| exon 4 | 1150 | 114 | Gly114Ala | | |
| exon 4 | 1152 | 115 | Arg115Gly | | |
| exon 4 | 1161 | 118 | Val118Leu | Val118insAAAC | |
| intron 4 | 1415 | | 1415t > g | | |
| exon 5 | 1441 | 124 | Asp124Gly | Asp124Val | |
| exon 5 | 1443 | 125 | Asp125His | | |
| exon 5 | 1446 | 126 | Leu26delTT | Leu26STOP | Leu26Ser |
| exon 5 | 1450 | 127 | Gly127insTGGG | | |
| exon 5 | 1465 | 132 | Glu132insTT | | |
| exon 5 | 1467 | 133 | Glu133del | | |
| exon 5 | 1471 | 134 | Ser134Asn | | |
| exon 5 | 1487 | 139 | Asn139Asn | Asn139Lys | |
| exon 5 | 1489 | 140 | Ala140Gly | Ala140Ala | |
| exon 5 | 1491 | 141 | Gly141STOP | | |
| exon 5 | 1501 | 144 | Leu144Ser | Leu144Phe | |
| exon 5 | 1503 | 145 | Ala145Thr | Ala145Gly | |
| exon 5 | 1506 | 146 | Cys146Arg | | |
| exon 5 | 1509 | 147 | Gly147Arg | | |
| exon 5 | 1512 | 148 | Val148Ile | Val148Gly | |
| exon 5 | 1516 | 149 | Ile149Thr | | |
| exon 5 | 1522 | 151 | Ile151Thr | Ile151Ser | |
| exon 5 | 1529 | 153 | Gln153Gln | | |

II. RNA Interference

The present invention features methods for suppressing or knocking down expression of proteins (e.g., gain-of-function mutant proteins). The methods of the invention employ novel RNAi agents which target both mutant and wild-type alleles of a gain-of-function gene (e.g. SOD1) using a sequence-specific RNA silencing mechanisms known as RNA interference (Hutvagner et al., 2002). After introduction of RNAi agent into cells, the agent binds to target site sequence in a site-specific manner (e.g., by RNAi) thereby halting expression of both forms of the target gene. The wild-type copy of the gain-of-function protein is provided in the form of a RNA silencing-resistant gene. Cells survive on the wild-type copy provided from the RNA silencing-resistant gene; this approach prevents the ravages of gain-of-function mutant by eliminating its production.

RNA interference or RNAi is a remarkably efficient process whereby double-stranded RNA (dsRNA) induces the sequence-specific degradation of homologous mRNA in animals and plant cells (Hutvagner and Zamore (2002), Curr. Opin. Genet. Dev., 12, 225-232; Sharp (2001), Genes Dev., 15, 485-490). In mammalian cells, RNAi can be triggered by ~21-nucleotide (nt) duplexes of small interfering RNA (siRNA) (Chiu et al. (2002), Mol. Cell., 10, 549-561; Elbashir et al. (2001), Nature, 411, 494-498), or by micro-RNAs (miRNA), functional small-hairpin RNA (shRNA), or other dsRNAs which are expressed in-vivo using DNA templates with RNA polymerase III promoters (Zeng et al. (2002), Mol. Cell, 9, 1327-1333; Paddison et al. (2002), Genes Dev., 16, 948-958; Lee et al. (2002), Nature Biotechnol., 20, 500-505; Paul et al. (2002), Nature Biotechnol., 20, 505-508; Tuschl, T. (2002), Nature Biotechnol., 20, 440-448; Yu et al. (2002), Proc. Natl. Acad. Sci. USA, 99(9), 6047-6052; McManus et al. (2002), RNA, 8, 842-850; Sui et al. (2002), Proc. Natl. Acad. Sci. USA, 99(6), 5515-5520.)

III. RNAi Agents

The present invention features RNAi agents (e.g., siRNA and shRNAs), methods of making said RNAi agents and methods (e.g., research and/or therapeutic methods) for using said RNAi agents (or portions thereof). The RNAi agents of the invention are duplex molecules (or molecules having duplex-like structure) comprising a sense strand and complementary antisense strand (or portions thereof), wherein antisense strand (or portions thereof) has sufficient complementary to a target sequence to mediate RNAi. The target sequence is shared by both mutant and wild-type variants of an target mRNA molecule (e.g., a target mRNA corresponding to a gain-of-function gene). Accordingly, the RNAi agents of the invention are capable of mediating RNAi of both the mutant and wild-type variants of the target mRNA molecule.

a) siRNA Molecules

An siRNA molecule of the invention is a duplex consisting of a sense strand and complementary antisense strand, the antisense strand having sufficient complementary to a target mRNA to mediate RNAi. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed or aligned. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region e.g., a gain-of-function gene target region, common to both the wild type and mutant allele of a gain of function gene and the other strand is identical or substantially identical to the first strand.

Generally, siRNA molecules can be designed using method well-known in the art. In an exemplary embodiment, the siRNA molecules are designed using the following protocol:

1. A target sequence is selected (e.g., a mutant allele or mRNA) having a gain-of-function mutation (e.g. a single nucleotide mismatch, for example a point mutation) as compared to a reference sequence (e.g. a wild type allele or mRNA sequence) A portion of the target sequence, i.e. the target site, is selected that does not include the mutation. Preferably the siRNA is designed such that the target site is distant from the site of the mutation. The phrase "distant" means that there are the same number of nucleotides (i.e., 8, 9, 10, 11 or 12) between the mutation and the target site. Preferably, the target site is identical or substantially identical between the mutant and reference sequence.

In preferred embodiments, the target site comprises an AA dinucleotide sequence with 16 or more 3' adjacent nucleotides. In one embodiment, the nucleic acid molecules are selected from a region of the target sequence beginning at least 50 to 100 nt downstream of the start codon, e.g., of the sequence of SOD1. Further, siRNAs with lower G/C content (35-55%) may be more active than those with G/C content higher than 55%. Thus in one embodiment, the target site has a high (e.g. 35-55%) G/C content.

2. The sense strand of the siRNA is designed based on the sequence of the selected target site. Preferably the sense strand includes about 19 to 25 nucleotides, e.g., 19, 20, 21, 22, 23, 24 or 25 nucleotides. More preferably, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNAi agents have been demonstrated to elicit an interferon or PKR response in certain mammalian cells which may be undesirable. Preferably the RNAi agents of the invention do not elicit a PKR response (i.e., are of a sufficiently short length). However, longer RNAi agents may be useful, for example, in cell types incapable of generating a PRK response or in situations where the PKR response has been down-regulated or dampened by alternative means.

The siRNA molecules of the invention have sufficient complementarity with the target site such that the siRNA can mediate RNAi. Accordingly, in a preferred embodiment, the sense strand of the siRNA is designed have to have a sequence sufficiently identical to a portion of the target. For example, the guide strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. In another embodiment, the sense strand of the siRNA has perfect identity with the target site. In another embodiment, the sense strand has 4, 3, 2, 1, or 0 mismatched nucleotide(s) with the target site. Moreover, siRNA sequences with small insertions or deletions of 1 or 2 nucleotides may also be effective for mediating RNAi.

Sequence identity may determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions ×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation. Further general information about the design and use of siRNA may be found in "The siRNA User Guide," available at The Max-Plank-Institut für Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

The design of siRNAs suitable for targeting the SOD1 is described in detail herein. SOD1 siRNA target regions of SOD1 common to both mutant and wild-type SOD1 (i.e., regions present in the sequence set forth in Table 1 supra but distinct from those listed in Table 2 supra). In one embodiment, the siRNA molecule of the invention may comprise a first strand comprising a sequence with sufficient complementarity to any of the target site sequences listed in Table 3 infra. In a preferred embodiment, an siRNA molecule of the present invention comprises SEQ ID NO:2 or SEQ ID NO: 6. In an exemplary embodiment, the siRNA comprises SEQ ID NO:1, (sense strand) and SEQ ID NO:2 (anti-sense or guide strand). In another exemplary embodiment, the siRNA comprises SEQ ID NO:5 (sense strand) and SEQ ID NO:6 (anti-sense or guide strand).

TABLE 3 siRNA Target Sequences in SOD1

| siRNA Target Sequence | SEQ ID NO: | Start | GC content |
| --- | --- | --- | --- |
| TCATCAATTTCGAGCAGAA | 9 | 117 | 36.84% |
| TTCGAGCAGAAGGAAAGTA | 10 | 125 | 42.11% |
| GGAAGCATTAAAGGACTGA | 11 | 164 | 42.11% |
| AAGCATTAAAGGACTGACT | 12 | 166 | 36.84% |
| GCATTAAAGGACTGACTGA | 13 | 168 | 42.11% |
| ACTGACTGAAGGCCTGCAT | 14 | 178 | 52.63% |
| TCCTCACTTTAATCCTCTA | 15 | 250 | 36.84% |
| GGCAATGTGACTGCTGACAAAG | 1 | 256 | 50.00% |
| GCCGATGTGTCTATTGAAGAT | 5 | 286 | 42.86% |
| GCAATGTGACTGCTGACAA | 16 | 321 | 47.37% |
| CCGATGTGTCTATTGAAGA | 17 | 351 | 42.11% |
| CGATGTGTCTATTGAAGAT | 18 | 352 | 36.84% |
| TATTGAAGATTCTGTGATC | 19 | 361 | 31.58% |
| TGGAAGTCGTTTGGCTTGT | 20 | 487 | 47.37% |
| GGAAGTCGTTTGGCTTGTG | 21 | 488 | 52.63% |
| TTGCTTTAAAGTACCTGTA | 22 | 654 | 31.58% |
| TAAAGTACCTGTAGTGAGA | 23 | 660 | 36.84% |
| CCAGACTTAAATCACAGAT | 24 | 760 | 36.84% |
| GCAGTTATTATGAGGCTAT | 25 | 839 | 36.84% |

(the skilled artisan will appreciate that the SOD1 target sequences are the same as the sequences depicted above, but for the presence of uracil (U) in the place of thymine (T))

In certain embodiments, only the antisense strand of the a siRNA molecule (ie. a ss-RNAi) of the invention is employed. Because RNAi is believed to progress via at least one single-stranded RNA intermediate, the skilled artisan will appreciate that ss-siRNAs utilized according to any of the methodologies described herein.

b) Short Hairpin RNA (shRNA) Molecules

In certain featured embodiments, the instant invention provides shRNAs capable of mediating RNAi of a gain-of-function target mRNA. In contrast to siRNAs, shRNAs mimic the natural precursors of micro RNAs (miRNAs). miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired RNAi agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

In preferred embodiments, the shRNA molecules of the invention are designed to produce any of the siRNAs described supra when processed in a cell e.g., by Dicer present within the cell. The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that, has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

One strand of the stem portion of the shRNA is further sufficiently complementary (e.g., antisense) to a target RNA (e.g., mRNA) sequence to mediate degradation or cleavage of said target RNA via RNA interference (RNAi). The antisense portion can be on the 5' or 3' end of the stem. The stem portions of a shRNA are preferably about 15 to about 50 nucleotides in length. Preferably the two stem portions are about 18 or 19 to about 25, 30, 35, 37, 38, 39, or 40 or more nucleotides in length. When used in mammalian cells, the length of the stem portions should be less than about 30 nucleotides to avoid provoking non-specific responses like the interferon pathway. In non-mammalian cells, the stem can be longer than 30 nucleotides. In fact, a stem portion can include much larger sections complementary to the target mRNA (up to, and including the entire mRNA). The two portions of the duplex stem must be sufficiently complementary to hybridize to form the duplex stem. Thus, the two portions can be, but need not be, fully or perfectly complementary.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the invention include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA (e.g., SOD1 mRNA), for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR, provided said portion is distant from the site of the gain-of-function mutation. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor, and to maximize the efficacy of the resulting siRNA in targeting the corresponding mRNA for translational repression or destruction by RNAi in vivo and in vitro.

shRNAs so generated are processed under appropriate conditions (e.g., in an appropriate in vitro reaction or in a cell) by RNAi machinery (i.e., Dicer and/or RISC complexes) to generate siRNAs. shRNAs can be synthesized exogenously or can be transcribed in vivo from an RNA polymerase (e.g., a Pol II or Pol III polymerase), thus permitting the construction of continuous cell lines or transgenic animals in which the desired gene silencing is stable and heritable.

In one embodiment, the shRNA molecule of the invention may comprise a sequence with sufficient complementarity to any of the target site sequences listed in Table 3. In a preferred embodiment, an shRNA molecule of the present invention comprises SEQ ID NO:2 or SEQ ID NO: 6. In an exemplary embodiment, the shRNA is hSOD1hp-1 or a precursor thereof comprising SEQ ID NO:1, (sense strand) and SEQ ID NO:2 (anti-sense or guide strand). In another exemplary embodiment, the shRNA hSOD1hp-3 or a precursor thereof comprising SEQ ID NO:5 (sense strand) and SEQ ID NO:6 (anti-sense or guide strand).

c. Production of RNAi Agents

RNAi agents may (e.g., siRNAs) be produced enzymatically or by partial/total organic synthesis, any modified ribonucleotide can be introduced by in vitro enzymatic or organic synthesis. In one embodiment, a RNAi agent is prepared chemically. Methods of synthesizing RNA molecules are known in the art, in particular, the chemical synthesis methods as described in Verma and Eckstein (1998) *Annul Rev. Biochem.* 67:99-134.

In one embodiment, a RNAi agent is prepared enzymatically. For example, a siRNA molecule can be prepared by enzymatic processing of a long ds RNA having sufficient complementarity to the desired target mRNA. Processing of long ds RNA can be accomplished in vitro, for example, using appropriate cellular lysates and siRNA can be subsequently purified by gel electrophoresis or gel filtration. siRNA can then be denatured according to art-recognized methodologies. In an exemplary embodiment, RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the RNA can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol.* 180:51-62). The RNA may be dried for storage or dissolved in an aqueous solution. The solution may contain buffers or salts to inhibit annealing, and/or promote stabilization of the single strands.

Certain RNAi agents of the invention, in particular siRNA molecules of the invention, can also be prepared in vivo by enzymatic processing of a long dsRNA molecule (>30 b.p.) which has sufficient complementarity to the desired target mRNA. Preferably, in vivo processing of the long dsRNA molecule occurs in a non-mammalian cell or a mammalian cell which is deficient in the interferon-mediated inflammatory response to dsRNA. In one embodiment, the cell capable of dsRNA enzymatic processing may be present within an organism such that dsRNA processing can be induced in vivo to trigger gene silencing of a target gene within the organism. Alternatively, the cell (i.e. a host cell) containing endogenous machinery for dsRNA processing (e.g. DICER) or transformed with heterologous genes to enable dsRNA processing) be cultured and induced to process dsRNA in vitro. RNA silencing agents may then be purified from the host cell following dsRNA processing for administration to an organism containing the target gene to be silenced.

In another embodiment, RNAi are synthesized directly either in vivo, in situ, or in vitro. An endogenous RNA polymerase in the cell may mediate transcription of the RNAi agent in vivo or in situ, or a cloned RNA polymerase can be used for transcription of the RNAi agent in vivo or in vitro. For transcription from a transgene in vivo or an expression construct, a regulatory region (e.g., promoter, enhancer, silencer, splice donor and acceptor, polyadenylation) may be used to transcribe the RNAi agent (e.g. siRNA or or shRNA).

Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses a RNAi agent (e.g. siRNA or shRNA) from a recombinant construct may be produced by introducing the construct into a zygote, an embryonic stem cell, or another multipotent cell derived from the appropriate organism.

d. Modified RNAi Agents

The RNAi agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features RNAi agents that include first and second strands wherein the second strand and/or first strand is modified by the substitution of internal nucleotides with modified nucleotides, such that in vivo stability is enhanced as compared to a corresponding unmodified RNAi agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a preferred embodiment of the present invention the RNAi agents may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNAi agent, for example, to increase half-life in the body. Thus, the invention includes RNAi agents that include RNAi agents having two complementary strands of nucleic acid, such that the two strands are crosslinked.

The RNAi agents of the invention can be unconjugated or can be conjugated (e.g., at its 3' terminus) to another moiety (e.g. a non-nucleic acid moiety such as a nanoparticle, a peptide, an organic compound (e.g., a dye), or the like), to enhance a property of the composition, e.g., cellular uptake, cellular targeting, or pharmacokinetic parameters such as absorption, efficacy, bioavailability, and/or half-life. Modifying RNAi agents in this way may be useful for tracing movement of the agent in a cell, or improve the stability of the modified agent as compared to the unmodified agent.

The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The RNAi agents of the present invention can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the agent can be radiolabeled, e.g., using $^3$H, $^{32}$P, or other appropriate isotope.

The RNAi agents of the invention can also altered to facilitate enhanced efficacy and specificity in mediating RNAi. Such methods involve facilitating entry of the antisense strand of the siRNA (e.g., a siRNA designed using the methods of the invention or an siRNA produced from a shRNA) into RISC in favor of the sense strand and thus increasing or improving the efficiency of target cleavage and silencing. In particular, the base pair strength between the 5' end of the sense strand and 3' end of the antisense strand can be altered, e.g., lessened or reduced, as described in detail in International Publication No. WO 2005/001045, the contents of which are incorporated in their entirety by this reference. In one embodiment of these aspects of the invention, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. Preferably, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). Preferably, the base pair is selected from the group consisting of an I:A, I:U and I:C. In yet another embodiment, the base pair strength is less due to at least one base pair comprising a modified nucleotide. In preferred embodiments, the modified nucleotide is selected from the group consisting of 2-amino-G, 2-amino-A, 2,6-diamino-G, and 2,6-diamino-A.

e. Detection of RNAi Agents

In certain aspects of the invention, it may be important to detect the generation or expression of RNAi agents (e.g. siRNAs and shRNAs), target mRNAs and/or the gene products encoded by said target RNAs. The detection methods used herein include, for example, cloning and sequencing, ligation of oligonucleotides, use of the polymerase chain reaction and variations thereof (e.g., a PCR that uses 7-deaza GTP), use of single nucleotide primer-guided extension assays, hybridization techniques using target-specific oligonucleotides that can be shown to preferentially bind to complementary sequences under given stringency conditions, and sandwich hybridization methods.

Sequencing may be carried out with commercially available automated sequencers utilizing labeled primers or terminators, or using sequencing gel-based methods. Sequence analysis is also carried out by methods based on ligation of oligonucleotide sequences which anneal immediately adjacent to each other on a target DNA or RNA molecule (Wu and Wallace, Genomics 4: 560-569 (1989); Landren et al., Proc. Natl. Acad. Sci. 87: 8923-8927 (1990); Barany, F., Proc. Natl. Acad. Sci. 88: 189-193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating late onset diabetes mutation loci. The elevated reaction temperatures permits the ligation reaction to be conducted with high stringency (Barany, F., PCR Methods and Applications 1: 5-16 (1991)).

The hybridization reactions may be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

Detection oligonucleotide probes range in size between 10-1,000 bases. In order to obtain the required target discrimination using the detection oligonucleotide probes, the hybridization reactions are generally run between 20°-60° C., and most preferably between 30°-50° C. As known to those skilled in the art, optimal discrimination between perfect and mismatched duplexes is obtained by manipulating the temperature and/or salt concentrations or inclusion of formamide in the stringency washes.

Detection of proteins may be carried out using specific antibodies, e.g., monoclonal or polyclonal antibodies, or fragments thereof.

Preferred detection reagents are labeled, e.g., fluorescents, coloro-metrically or radio-iso-typically labeled to facilitate visualization and/or quantitation.

III. RNAi-Resistant Replacement Genes

Another aspect of the invention pertains to RNAi resistant replacement genes. These RNAi-resistant replacement genes contain mismatches with their respective RNA silencing agents and are resistant to the RNA silencing induced by their respective RNA silencing agents. Accordingly, the RNAi-resistant replacement genes provide for the functional replacement of any wild-type gain-of-function target mRNA sequence that may be by degraded by the cognate RNAi agent.

RNAi resistant replacement genes of the present invention can be designed as follows. An RNA silencing agent (e.g. siRNA or shRNA) is designed as described above. A sequence corresponding target site (e.g., cDNA or mRNA sequence) is studied for the possible introduction of one or more silent mutations. The term "silent mutation as defined herein refers to a base change in a coding region that does not affect the amino acid that is encoded due to the degeneracy of the genetic code. A candidate site of the introduction of a silent mutation is nucleotide position in the target sequence that corresponds to a degenerate codon in the open reading frame of the mRNA encoded by the target gene. For example, the change UGC UGU in the target mRNA is silent because both are codons for cysteine. Introduction of a silent mutation into a target gene sequence or cDNA encoding the wild-type form of the target mRNA results in a mismatch which decreases the complementarity between the target sequence and the siRNA, making the sequence less susceptible to RNAi-induced degradation. By increasing the number of silent mutations in the target sequence, the wild-type target mRNA is made increasingly resistant to RNAi. Accordingly, the wild-type target mRNAs encoded by the RNAi-replacement genes of the invention lack sufficient complementarity with the RNAi agent. Thus, the RNAi resistant replacement gene is capable of wild-type gene rescue.

The RNAi-replacement gene is designed such that the encoded target sequence has less than 100% identity with the sense strand of the RNAi agent. Preferably the target sequence has less than 80% identity, e.g., 80%, 75%, 70%, 60%, 50%. In certain embodiments, the target sequence encoded by the RNAi-replacement gene has more than 1 silent mutation. e.g. 2, 3, 4, 5, 6, 7 or more silent mutations. In preferred embodiments, the RNAi replacement gene has more than 4 silent mutations.

The RNAi replacement gene may be tested experimentally for its ability to hybridize with the RNAi agent using methods well known in the art. Alternatively, a Northern Blot can be used to confirm that the mRNA encoded by the RNAi replacement gene is susceptible to RNAi.

RNAi resistant replacement genes of the present invention can be designed according to the above exemplary teachings for any region found in the SOD1 gene encoding wild-type function. Moreover, the technology is applicable to targeting any other disease gene, in particular, gain-of-function mutant genes.

In certain exemplary embodiments, the SOD1 RNAi resistant replacement gene of the invention may comprise any of the RNAi resistant target gene sequences listed in Table 4 infra. In an exemplary embodiment, a SOD1 RNAi resistant replacement gene comprises SEQ ID NO:3 or SEQ ID NO: 8.

TABLE 4

SOD1 RNAi Resistant Replacement Genes

| Specific siRNAs Target Sequence of SOD1 | SEQ ID NO. | RNAi Resistant Target Gene Sequence | SEQ ID NO. |
|---|---|---|---|
| 5-GGCAATGTGACTGCTGACAAAG-3 | 1 | 5-GGAAACGTCACGGCGGATAAAG-3 | 3 |
| 5-GCCGATGTGTCTATTGAAGAT-3 | 5 | 5-GCAGACGTCAGTATAGAGGAC-3 | 8 |
| 5-TCATCAATTTCGAGCAGAA-3 | 9 | 5-TCATCAATTTCGAGCAGAA-3 | 9 |
| | | 5-TCATTAACTTTGAACAAAA-3 | 26 |
| | | 5-TCATAAATTTCGAGCAGAA-3 | 27 |
| 5-TTCGAGCAGAAGGAAAGTA-3 | 10 | 5-TTCGAGCAGAAGGAAAGTA-3 | 10 |
| | | 5-TTTGAACAAAAAGAGACA-3 | 28 |
| 5-GGAAGCATTAAAGGACTGA-3 | 11 | 5-GGAAGCATTAAAGGACTGA-3 | 11 |
| | | 5-GGTAGTATCAAGGGTCTTA-3 | 29 |
| | | 5-GGCAGCATAAAAGGCCTCA-3 | 30 |
| | | 5-GGGAGCATTAAAGGGCTAA-3 | 31 |
| 5-AAGCATTAAAGGACTGACT-3 | 12 | 5-AAGCATTAAAGGACTGACT-3 | 12 |
| | | 5-AAGTATCAAGGGTCTTACC-3 | 32 |
| | | 5-AAGCATAAAAGGGGCTCACA-3 | 33 |
| | | 5-AAGCATTAAAGGCCTAACG-3 | 34 |
| 5-GCATTAAAGGACTGACTGA-3 | 13 | 5-GCATTAAAGGACTGACTGA-3 | 13 |
| | | 5-GCATCAAGGGTCTTACCGA-3 | 35 |
| | | 5-GCATAAAAGGCCTCACAGA-3 | 36 |
| | | 5-GCATTAAAGGGCTAACGGA-3 | 37 |
| 5-ACTGACTGAAGGCCTGCAT-3 | 14 | 5-ACTGACTGAAGGCCTGCAT-3 | 14 |
| | | 5-ACTTACCGAGGGTCTTCAC-3 | 38 |
| | | 5-ACTCACAGAAGGACTCCAT-3 | 39 |
| | | 5-ACTAACGGAAGGGCTACAT-3 | 40 |
| 5-TCCTCACTTTAATCCTCTA-3 | 15 | 5-TCCTCACTTTAATCCTCTA-3 | 15 |
| | | 5-TCCCCATTTCAACCCCCTT-3 | 41 |
| | | 5-TCCACACTTTAATCCACTG-3 | 42 |
| | | 5-TCCGCACTTTAATCCGCTC-3 | 43 |
| 5-GCAATGTGACTGCTGACAA-3 | 16 | 5-GCAATGTGACTGCTGACAA-3 | 16 |
| | | 5-GCAACGTTACCGCCGATAA-3 | 44 |
| | | 5-GCAATGTCACAGCAGACAA-3 | 45 |
| | | 5-GCAATGTAACGGCGGACAA-3 | 46 |

TABLE 4-continued

SOD1 RNAi Resistant Replacement Genes

| Specific siRNAs Target Sequence of SOD1 | SEQ ID NO. | RNAi Resistant Target Gene Sequence | SEQ ID NO. |
|---|---|---|---|
| 5-CCGATGTGTCTATTGAAGA-3 | 17 | 5-CCGATGTGTCTATTGAAGA-3 | 17 |
| | | 5-CCGACGTTTCCATCGAGGA-3 | 47 |
| | | 5-CCGATGTCTCAATAGAAGA-3 | 48 |
| | | 5-CCGATGTATCGATTGAAGA-3 | 49 |
| 5-CGATGTGTCTATTGAAGAT-3 | 18 | 5-CGATGTGTCTATTGAAGAT-3 | 18 |
| | | 5-CGACGTTTCCATCGAGGAC-3 | 50 |
| | | 5-CGATGTCTCAATAGAAGAT-3 | 51 |
| | | 5-CGATGTATCGATTGAAGAT-3 | 52 |
| 5-TATTGAAGATTCTGTGATC-3 | 19 | 5-TATTGAAGATTCTGTGATC-3 | 19 |
| | | 5-TATCGAGGACTCCGTTATT-3 | 53 |
| | | 5-TATAGAAGATTCAGTCATA-3 | 54 |
| | | 5-TATTGAAGATTCGGTAATC-3 | 55 |
| 5-TGGAAGTCGTTTGGCTTGT-3 | 20 | 5-TGGAAGTCGTTTGGCTTGT-3 | 20 |
| | | 5-TGGTAGCCGCTTAGGCTGC-3 | 56 |
| | | 5-TGGCAGTCGATTGGCATGT-3 | 57 |
| | | 5-TGGGAGTCGGTTGGCGTGT-3 | 58 |
| 5-GGAAGTCGTTTGGCTTGTG-3 | 21 | 5-GGAAGTCGTTTGGCTTGTG-3 | 21 |
| | | 5-GGTAGCCGCTTAGCCTGCG-3 | 59 |
| | | 5-GGCAGTCGATTGGCATGTG-3 | 60 |
| | | 5-GGGAGTCGGTTGGCGTGTG-3 | 61 |
| 5-TTGCTTTAAAGTACCTGTA-3 | 22 | 5-TTGCTTTAAAGTACCTGTA-3 | 22 |
| | | 5-TTGCCTTGAAATATCTATA-3 | 62 |
| | | 5-TTGCATTAAAGTACCTGTA-3 | 63 |
| | | 5-TTGCGTTAAAGTACCTGTA-3 | 64 |
| 5-TAAAGTACCTGTAGTGAGA-3 | 23 | 5-TAAAGTACCTGTAGTGAGA-3 | 23 |
| | | 5-TAAAATATCTTTAATGAGA-3 | 65 |
| | | 5-TAAAGTACCTCTAGTGAGA-3 | 66 |
| | | 5-TAAAGTACCTATAGTGAGA-3 | 67 |
| 5-CCAGACTTAAATCACAGAT-3 | 24 | 5-CCAGACTTAAATCACAGAT-3 | 24 |
| | | 5-CCAAACCTAGATTACTGAC-3 | 68 |
| | | 5-CCAGACATAAATAACCGAT-3 | 69 |
| | | 5-CCAGACGTAAATCACGGAT-3 | 70 |
| 5-GCAGTTATTATGAGGCTAT-3 | 25 | 5-GCAGTTATTATGAGGCTAT-3 | 25 |
| | | 5-GCTGTCATCATGAGACTTT-3 | 71 |
| | | 5-GCCGTAATAATGAGGCTCT-3 | 72 |
| | | 5-GCGGTGATTATGAGGCTGT-3 | 73 |

IV. Constructs and Host Cells

Another aspect of the invention pertains to constructs, preferably expression constructs, encoding an RNAi agent (e.g. an siRNA or shRNA) and/or a RNAi-replacement gene of the present invention (or a portion thereof). Expression constructs include any construct suitable for use in the appropriate expression system and include, but are not limited to, retroviral vectors, linear expression cassettes, plasmids and viral or virally-derived vectors, as known in the art. In one embodiment, the construct is a transgene. In another embodiment, the construct is a vector. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The vectors described herein can be introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by reference. See, also, Ausubel et al., Current Protocols in Molecular Biology, John Wiley and Sons, Baltimore, Md. (1989); Hitt et al, "Construction and propagation of human adenovirus vectors," in Cell Biology: A Laboratory Handbook, Ed. J. E. Celis., Academic Press. 2.sup.nd Edition, Volume 1, pp: 500-512, 1998; Hitt et al, "Techniques for human adenovirus vector construction and characterization," in Methods in Molecular Genetics, Ed. K. W. Adolph, Academic Press, Orlando, Fla., Volume 7B, pp:12-30, 1995; Hitt, et al., "Construction and propagation of human adenovirus vectors," in Cell Biology: A Laboratory Handbook," Ed. J. E. Celis. Academic Press. pp:479-490, 1994, also hereby incorporated by reference. The methods include, for example, stable or transient transfection, lipofection (e.g., cationic liposome transfection), electroporation and infection with recombinant viral vectors.

In certain embodiments, the expression constructs of the invention comprise a nucleic acid (DNA or RNA) operably linked to one or more regulatory sequences (e.g., promoter sequences). The phrase "operably linked" is intended to mean that the nucleotide sequence of interest (e.g., a sequence encoding an RNAi agent (e.g. shRNA) or RNAi replacement gene) is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences).

Other elements included in the design of a particular expression vector can depend on such factors as the choice of the host cell to be transformed, the level of expression of protein desired, etc. The expression vectors of the invention can be introduced into host cells to thereby produce mRNA, proteins or peptides, including fusion proteins or peptides, encoded by nucleic acids as described herein.

Constructs can be constructed by recombinant DNA technology methods known in the art. The nucleic acid sequences encoding the RNAi agents or RNAi replacement gene can be prepared using known techniques. For example, two synthetic DNA oligonucleotides can be synthesized to create a novel gene encoding an entire RNAi agent. The DNA oligonucleotides, which will pair, leaving appropriate 'sticky ends' for cloning, can be inserted into a restriction site in a plasmid that contains a promoter sequence (e.g., a Pol II or a Pol III promoter) and appropriate terminator sequences 3' to the engineered RNA precursor sequences (e.g., a cleavage and polyadenylation signal sequence from SV40 or a Pol III terminator sequence).

The constructs described herein can be introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by reference. See, also, Ausubel et al., Current Protocols in Molecular Biology, John Wiley and Sons, Baltimore, Md. (1989); Hitt et al, "Construction and propagation of human adenovirus vectors," in Cell Biology: A Laboratory Handbook, Ed. J. E. Celis., Academic Press. 2.sup.nd Edition, Volume 1, pp: 500-512, 1998; Hitt et al, "Techniques for human adenovirus vector construction and characterization," in Methods in Molecular Genetics, Ed. K. W. Adolph, Academic Press, Orlando, Fla., Volume 7B, pp:12-30, 1995; Hitt, et al., "Construction and propagation of human adenovirus vectors," in Cell Biology: A Laboratory Handbook," Ed. J. E. Celis. Academic Press. pp:479-490, 1994, also hereby incorporated by reference. The methods include, for example, stable or transient transfection, lipofection (e.g., cationic liposome transfection), electroporation and infection with recombinant viral vectors.

a. RNAi Agent Expression Constructs

In certain embodiments, the invention provides DNA expression constructs which facilitate the expression of the RNAi agents (e.g. siRNAs and shRNAs) of the invention.

To achieve intracellular concentrations of the RNAi agent sufficient to suppress expression of target mRNAs, one can use, for example, such expression constructs can include one or more inducible promoter systems, for example RNA Poly II or RNA Pol III (e.g. U6 or H1) promoter systems. The use of such a construct to transfect target cells in vitro or in vivo will result in the transcription of sufficient amounts of the RNAi agent that can target a corresponding mRNA sequence for cleavage (i.e. RNAi). For example, a vector can be introduced in vivo such that it is taken up by a cell and directs the transcription of an RNAi agent. Such a vector can remain episomal or become chromosomally integrated, as long as it can be transcribed to produce the desired stRNA precursor.

In certain embodiments, the expression constructs of the invention encode an siRNA. The expression constructs preferably encode or both strands of an siRNA. Expression constructs expressing both strands can also include loop structures linking both strands. Alternatively, each strand can be separately transcribed from separate promoters within the same construct. Each strand can also be transcribed from a separate expression construct. (Tuschl (2002), supra).

In other embodiments, a construct that expresses a shRNA of the invention an be used to produce siRNAs to initiate RNAi against specific mRNA targets in mammalian cells (Zeng (2002), supra). Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides. Brummelkamp et al., Science 296:550-553 (2002); Lee et al, (2002). supra; Miyagishi and Taira, Nature Biotechnol. 20:497-500 (2002); Paddison et al. (2002), supra; Paul (2002), supra; Sui (2002) supra; Yu et al. (2002), supra.

A single construct may contain multiple sequences coding for RNAi agents (e.g. siRNAs), such as multiple regions of the gene encoding mutant SOD1, targeting the same gene or multiple genes, and can be driven, for example, by separate PolIII promoter sites.

Viral-mediated delivery mechanisms can also be used to induce specific silencing of targeted genes through expression of RNAi agents, for example, by generating recombinant adenoviruses expression RNAi agents under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the RNAi agent results in in-vivo reduction of target gene expression. Id. In an animal model, whole-embryo electroporation can efficiently deliver synthetic nucleic acids into post-implantation mouse embryos (Calegari et al., Proc. Natl. Acad. Sci. USA 99(22): 14236-40 (2002)). In adult mice, efficient delivery of nucleic acid agents can be accomplished by "high-pressure" delivery technique, a rapid injection (within 5 seconds) of a large volume of nucleic acid agent containing solution into animal via the tail vein (Liu (1999), supra; McCaffrey (2002), supra; Lewis, Nature Genetics 32:107-108 (2002)).

b. RNAi-Resistant Gene Expression Constructs

In certain embodiments, the invention provides DNA expression constructs which facilitate the expression of an RNAi-resistant gene. For example, a vector can be introduced in vivo such that it is taken up by a target cell and directs the transcription of the RNAi-resistant gene. Such a vector can remain episomal or become chromosomally integrated, as long as it can be transcribed to produce the desired stRNA precursor. A single construct may contain a single copy or multiple copies of the RNAi-resistant gene.

c. Co-Expression Constructs

In certain embodiments, the invention provides DNA expression constructs which facilitate the expression of both an RNAi agent and a RNAi-resistant gene. In preferred embodiments, the vector directs the transcription and/or translation of both the RNAi-resistant gene and the RNAi agent in the same cell. Such agents are preferred as they ensure that functional replacement of the wild-type form of a target mRNA in a cell in which both the wild-type and mutant form of a gain-of-function target sequence have been degraded. Such a vector can remain episomal or become chromosomally integrated, as long as it can be transcribed to produce the desired RNAi agent and RNAi replacement gene. A single construct may contain a single copy or multiple copies of the RNAi-resistant gene and/or the RNAi agent.

d. Host Cells

Another aspect of the invention pertains to host cells into which a host construct of the invention has been introduced, i.e., a "recombinant host cell." It is understood that the term "recombinant host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell, although eukaryotic cells are preferred. Exemplary eukaryotic cells include mammalian cells (such as Chinese hamster ovary cells (CHO) or COS cells). Other suitable host cells are known to those skilled in the art.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders, such as disease and disorders associated with mutant or aberrant gene expression, gain-of-function mutants and neurological diseases and disorders.

The present invention is also not limited to the use of the cell types and cell lines used herein. Cells from different tissues or different species (human, mouse, etc.) are also useful in the present invention.

V. Methods of Introducing Nucleic Acids, Vectors, and Host Cells

Physical methods of introducing nucleic acids include injection of a solution containing the nucleic acid, bombardment by particles covered by the nucleic acid, soaking the cell or organism in a solution of the nucleic acid, or electroporation of cell membranes in the presence of the nucleic acid. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. The nucleic acid may be introduced along with other components that perform one or more of the following activities: enhance nucleic acid uptake by the cell or otherwise increase inhibition of the target gene.

Nucleic acids may be directly introduced into the cell (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of RNAi agent material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNAi agent may be introduced in an amount which allows delivery of at least one copy per cell. Higher doses (e.g., at least 5, 10, 100, 500 or 1000 copies per cell) of material may yield more effective inhibition; lower doses may also be useful for specific applications.

VI. Pharmaceutical Compositions and Methods of Administration

The RNAi agents, RNAi-replacement genes, and constructs of the present invention can be incorporated into pharmaceutical compositions. Such compositions typically include the nucleic acid molecule and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The compounds can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The compounds can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a nucleic acid molecule (i.e., an effective dosage) depends on the nucleic acid selected. For instance, if a plasmid encoding shRNA is selected, single dose amounts in the range of approximately 1:g to 1000 mg may be administered; in some embodiments, 10, 30, 100 or 1000:g may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

VI. Methods of Treatment

The present invention provides for both prophylactic and therapeutic methods of treating a subject at risk of (or susceptible to) a disease or disorder caused, in whole or in part, by a gain-of-function mutant protein. In one embodiment, the disease or disorder is a dominant gain-or-function disease. In a preferred embodiment, the disease or disorder is a disorder associated with the an alteration of SOD1 gene, specifically a point mutation in the SOD1 mutant allele, leading to a defect in SOD1 gene (structure or function) or SOD1 protein (structure or function or expression), such that clinical manifestations include those seen in ALS disease patients.

"Treatment", or "treating" as used herein, is defined as the application or administration of a therapeutic agent (e.g., a RNAi agent, RNAi-resistant replacement gene, or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., a RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., a RNAi agent, RNAi-resistant replacement gene, or vector or transgene encoding same) that is specific for a mutation within the gene, such that sequence specific interference with the gene is achieved. These methods can be performed in vitro (e.g., by culturing the cell with the agent) or, alternatively, in vivo (e.g., by administering the agent to a subject).

In certain preferred embodiments, the prophylactic and therapeutic methods of the invention comprise the administration of an RNAi agent or construct encoding same, together with a RNAi-resistant replacement gene or construct encoding same. In one embodiment, the RNAi agent and RNAi-resistant replacement are co-administered essentially simultaneously. In another embodiment, the RNAi agent and RNAi-resistant replacement gene are administered sequentially in any order. In preferred embodiments, the RNAi-resistant replacement gene is first administered to the patient to (ie. to ensure expression of the wild-type gain-of-function gene) followed by the RNAi agent some time later (e.g. 24 or 48 hours later).

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

EXAMPLES

The following materials, methods, and examples are illustrative only and not intended to be limiting.

Materials and Methods

In general, the practice of the present invention employs, unless otherwise indicated, conventional techniques of nucleic acid chemistry, recombinant DNA technology, molecular biology, biochemistry, and cell and cell extract preparation. See, e.g., *DNA Cloning*, Vols. 1 and 2, (D. N. Glover, Ed. 1985); *Oligonucleotide Synthesis* (M. J. Gait, Ed. 1984); *Oxford Handbook of Nucleic Acid Structure*, Neidle, Ed., Oxford Univ Press (1999); *RNA Interference: The Nuts & Bolts of siRNA Technology*, by D. Engelke, DNA Press, (2003); *Gene Silencing by RNA Interference: Technology and Application*, by M. Sohail, CRC Press (2004); Sambrook, Fritsch and Maniatis, *Molecular Cloning*: Cold Spring Harbor Laboratory Press (1989); and Current Protocols in Molecular Biology, eds. Ausubel et al., John Wiley & Sons (1992). See also PCT/US03/35009; which is incorporated in its entirety by reference herein.

shRNA Vector Preparation short-hairpin RNA (shRNA) vector constructed as described previously (Xia, et al., *Nucleic Acids Res.*, (2003), 31: e100). Briefly, the oligonucleotides comprising the sense strand, loop (TTCAAGAGA), antisense strand and the termination sequence (five Ts), with relevant restriction sites on flanking both 5' and 3' ends, were synthesized, annealed, and cloned downstream of a mouse U6 promoter in plasmids. These plasmids are then transfected into the cultured human cells to produce shRNA.

The sequences of the antisense strand of the shRNAs were:

```
                                           (SEQ ID NO: 75)
    shRNA-a:  5'-CUUUGUCAGCAGUCACAUUGC-3'

(SEQ ID NO: 76)
    shRNA-b:  5'-AUCUUCAAUAGACACAUCGGC-3'

(SEQ ID NO: 77)
    shRNA-c:  5'-UUUGUCAGCAGUCACAUUGCC-3'

(SEQ ID NO: 78)
    shRNA-d:  5'-UUGUCAGCAGUCACAUUGCC-3'

(SEQ ID NO: 79)
    shRNA-e:  5'-UUCACUGGUCCAUUACUUUCC-3'

(SEQ ID NO: 80)
    shRNA-f:  5'-GAACAUGGAAUCCAUGCAGGC-3'

(SEQ ID NO: 81)
    shRNA-g:  5'-AGUCAGUCCUUUAAUGCUUCC-3'

(SEQ ID NO: 82)
    shRNA-h:  5'-UUACACCACAAGCCAAACGAC-3'
```

Reporter: Target Gene Constructs

Fusion constructs encoding the human SOD1 target gene fused to a detectable reporter gene (firefly luciferase or green fluorescent protein (GFP)) were produced to evaluate silencing activity of each shRNA.

Human SOD1 cDNA was obtained by RT-PCR with total RNA from human embryonic kidney 293 (HEK293) cells and was cloned between KpnI and EcoRI sites of pcDNA3 (Clontech).

To create SOD 1-EGFP, EGFP coding sequences was PCR cloned from pEGFP-N1 vector (Clontech, Palo Alto, Calif., USA) and inserted between EcoRI and NotI sites of pcDNA3 vector, to create a pcDNA-EGFP vector. Human SOD1 and its various mutants were PCR cloned between KpnI and EcoRI sites of pcDNA3-EGFP vector.

To create luciferase-SOD1, the whole human SOD1 opening reading frame was PCR-cloned into the 3' untranslated region of luciferase, 100 basepairs downstream from firefly luciferase opening reading frame of a pGL2-control vector (Promega, Madison, Wis., USA). pRL-TK vector (Promega), which expresses renilla luciferase (Rr-luc), was used as transfection control.

GFP Fluorescence Analysis

Human embryonic kidney cell line 293 (HEK293) cells were grown in Dulbecco's Modi®ed Eagle's medium (DMEM) supplemented with 10% fetal bovine serum (FBS), 100 U/ml penicillin and 100 mg/ml streptomycin. Twenty-four hours before transfection, cells (70±90% confluency) were detached by trituration, transferred to 6-well plates and cultured in 10% FBS containing medium without antibiotics. The cells were transfected with 4 µg of the target vector SOD 1-GFP and 1-4 µg of each of the hairpin vectors using Lipofectamine 2000 (Invitrogen) according to the manufacturer's instructions. The transfection efficiency was ~95% in all experiments. After 24 h, the culture medium was changed to DMEM supplemented with 10% FBS and antibiotics. At 40 h after transfection, the cells were harvested and quickly frozen in liquid nitrogen.

The harvested cells were lysed in ice-cold reporter lysis buffer (Promega) containing protease inhibitors (complete, EDTAfree, 1 tablet/10 ml buffer; Roche Molecular Bio-chemicals, Indianapolis, Ind., USA). The lysate was cleared by centrifugation at 16000 g and 4° C. for 10 min. The total protein in the cleared lysate was measured using the Bbicinchoninic acid (BCA) assay (Pierce, Rockville, Ill., USA). The total protein concentration in each sample was adjusted to 0.5 mg/ml with the reporter buffer. Fluorescence of GFP in 140 ml of sample was measured by fluorescence spectroscopy (Photon Technology International, Lawrenceville, N.J., USA) with excitation at 460 nm and recording from 480 to 600 nm. The spectrum peak was detected at 502 nm, representing the fluorescence intensity of GFP. Fluorescence in the untransfected lysate was measured as background and subtracted from measurements of the transfected lysates.

Dual Luciferase Activity Assay

HEK 293 cells were transfected in 24-well culture plates using Lipofectamine 2000 (Invitrogen) according to the manufacturer's protocol. To each well, the amount of each plasmid was applied as follows: 0.25 ug of either shRNA-expressing vectors or the U6 blank vector, 0.25 ug of firefly luciferase (Pp-luc)-SOD1 vectors, and 0.15 ug of pRL-TK vector. Cells were harvested 28 hours after transfection. Luciferase activity in the cleared cell lysate was measured with the Dual Luciferase assay kit (Promega) using a Mediators Diagnostika (Vienna, Austria) PhL luminometer. The luciferase activity was defined as the ratio of Pp-luc to Rr-luc activities and expressed by normalization to the control, which was transfected with the blank vector plus two luciferase-expressing vectors.

Testing Cell Viability

Cells were split to 6-well plates at 800,000 cells per well, grown overnight and transfected with 4 ug of total vectors (shRNA:target=1:1). After 24 hours, the cells were transfected for the second time with the same amount of the vectors in the presence of 5% FBS. The cells were grown in DMEM supplemented with 10% FBS and antibiotics for another 24 hours. The cells were then triturated and distributed to 24-well plate at 150,000 cells per well. At 72 hours after the first transfection, the cells were treated with $H_2O_2$ (300 μM) for four hours. The media were then changed to the growth medium free of $H_2O_2$ for 20 hours.

Cell viability after $H_2O_2$ treatment was determined using a MTS assay according to manufacturer's instructions (Promega). The CellTiter 96® AQueous One Solution was directly added to growth medium and incubated for 4 hours before measuring absorbance at 495 nm with a 96 well plate reader. The absorbance of lysates was normalized to the average absorbance of the $H_2O_2$-untreated cells. Statistical analysis was performed using ANOVA followed by Turkey post hoc test to compare group means.

Western Blot

HEK 293 cells were transfected twice in 6-well plates at 0 and 24 hours, and split again at 48 hours. Seventy two hours after the first transfection, the cells were harvested for protein extraction. The cell pellets were lysed in ice-cold lysis buffer containing 0.4% NP-40, 0.2 mM $Na_3VO_4$, 20 mM HEPES (pH 7.9) and a cocktail of protease inhibitors (Complete-Mini, Sigma) by short sonication pulses. The lysate was cleared by centrifugation at 10,000 RCF for 10 min. Protein content was determined using BCA assay (Pierce). Fifty micrograms of total proteins were resolved on 15% SDS-PAGE gel and transferred onto GeneScreen Plus membrane (Perkin Elmer). SOD1 was detected with a sheep antibody (BioDesign) at 1:1000 dilution and SuperSignal kit (Pierce). The blot was photographed using the Kodak Digital Image Station 440CF.

Example 1

Generation of Optimal shRNA Sequences

Because more than one hundred SOD1 mutants cause ALS and the mutations are scattered throughout the entire coding sequence of SOD1, shRNAs targeting two different sequence regions are needed for silencing all mutants. To find the two optimal shRNAs, we constructed 8 shRNAs and tested them. To facilitate this test, we constructed a reporter construct, which consisted of firefly luciferase in the coding region and the entire SOD1 cDNA in the 3' untranslated region (luc-SOD1).

Each of the eight candidate shRNA vectors (as well as one empty control vector) were separately cotransfected with the luc-SOD1 reporter construct into HEK293 cells. The silencing activity by each of the shRNAs was measured by the dual luciferase assay. (see FIG. 2A). The luciferase activity represents the ratio of firefly luciferase activity to renilla luciferase activity, which was normalized to the average ratio from the cells transfected with the blank shRNA vector. Using this luciferase activity assay, we found two potent shRNAs, shRNA-a and shRNA-b comprising the antisense strand of SEQ ID NO: 75 and SEQ ID NO: 76, respectively. Both shRNAs inhibited luciferase activity by more than 95% (FIG. 2A). The location of the target site of each shRNA within the human SOD1 mRNA sequence is outlined in FIG. 2B.

Because the reporter luc-SOD1 altered the mRNA structure from the endogenous SOD1 mRNA, potent inhibition of the endogenous SOD1 expression by these shRNAs was not guaranteed. To test whether these two shRNAs could inhibit the endogenous SOD1 expression, we transfected these shRNAs into HEK293 cells and measured levels of endogenous human SOD1 by Western blot. We found that these two shRNAs potently inhibited the endogenous SOD1 expression, indicating that these shRNAs are fully active against the native SOD1 mRNA (FIG. 2C).

Example 2

Construction of SOD1 RNAi Resistant Replacement Genes

The following example describes methods for constructing an RNAi resistant rescue gene that expresses wild-type SOD1 in the presence of shRNA-induced silencing of a target allele.

The SOD1 RNAi resistant rescue gene i.e., hSOD1-1 and hSOD1-3 encodes the wild-type SOD1 with silent codon changes in the respective target regions of two SOD1 hairpins i.e., hSOD1hp-1 and hSOD1hp-3 (FIG. 3). The hSOD1-1 construct, GGAAACGTCACGGCGGATAAAG (sense stand; SEQ ID NO:3), contains 6 mismatched nucleotides (bold and underlined) against the hSOD1hp-1 target allele. The hSOD1-3 construct, GCAGACGTCAGTATAGAGGAC (sense strand; SEQ ID NO:8), contains 8 mismatched nucleotides (bold and underlined) against the hsSOD1-3 target allele.

Accordingly, hSOD1-1 and hSOD1-3 are resistant to shRNA-induced silencing by hSOD1hp-1 and hSOD1hp-3, respectively.

Example 3

SOD1 RNAi Resistant Replacement Gene Resistant to shRNA Induced Silencing by shRNA-a and shRNA-b To generate SOD1 RNAi-replacement genes that would resist cleavage by the potent shRNAs, of Example 1

(shRNA-a and shRNA-b) we created silent mutations in the cDNA sequence corresponding to the mRNA target site of shRNA-a (5'-GCAAUGUGACUGCUGACAAAG-3', SEQ ID NO: 83) and shRNA-b (5'-GCCGAUGUGUCUA-UUGAAGAU-3'; SEQ ID NO:84). We generated SOD1a, an RNAi-resistant replacement gene encoding a target mRNA sequence (5'-GCAACGUAACGGCUGACAAAG-3'; SEQ ID NO:85) having 3 mismatches, and SOD1b, an RNAi-resistant replacement gene encoding a target mRNA (5'-GC-CGACGUGAGUAUUGAAGAU; SEQ ID NO:86) having 3 mismatches (see FIG. 2B). Silent mutations of wildtype human SOD1 was generated using Quick-change Site-Directed Mutagenesis kit (Stratagene) to generate SOD1a and SOD1b.

The test resistance of the SOD1 RNAi resistant replacement gene against shRNA induced silencing, we generated GEP reporter genes by fusing SOD1wt, SOD1a and SOD1b genes at the N-terminus, with GFP gene at the C-terminus. To test these genes, we generated reporter genes by fusing SOD1wt, SOD1a and SOD1b genes at the N-terminal, with GFP gene at the C-terminal. These constructs were cotransfected into HEK293 cells. As expected, both shRNA-a and shRNA-b inhibited expression of SOD1wt-GFP potently (see FIG. 4A). However, SOD1a-GFP resisted RNAi by shRNA-a but not by shRNA-b (FIG. 4B) and SOD1b-GFP resisted RNAi by shRNA-b but not by shRNA-a (FIG. 4C). Furthermore, both shRNAs could efficiently silence the mutant gain-of-function genes $SOD^{G93A}$ (FIG. 4D) and $SOD1^{G85R}$ (FIG. 4E). Thus, the constructs worked as predicted.

Example 4

SOD1 RNAi Resistant Replacement Gene Resistant to shRNA Induced Silencing by shRNA-a and shRNA-b To determine whether shRNA-a and shRNA-b could reduce the function of SOD1, and whether their respective RNAi-resistant SOD1 genes could replace the SOD1 function reduced by these two shRNAs we evaluated the cell viability of cells infected with only with shRNAs as well as cells treated with shRNAs and rescued with the RNAi resistant replacement genes of Example 3.

Figure 5:
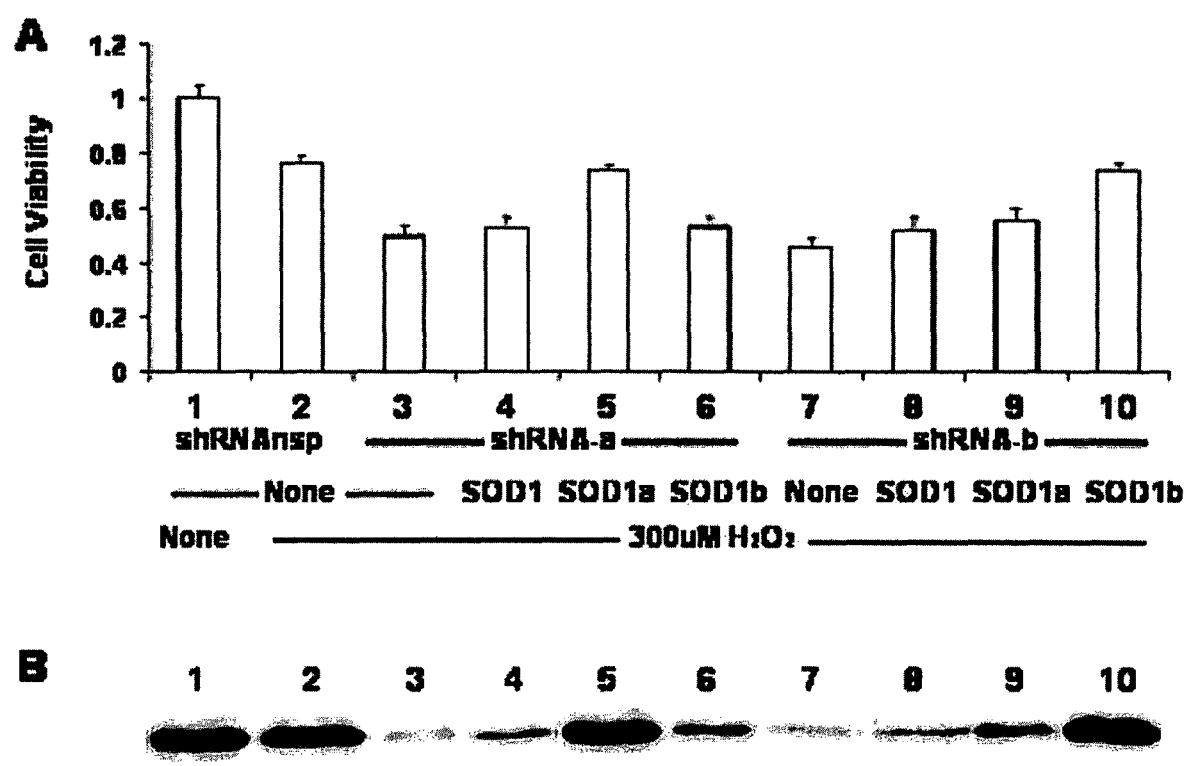
FIG. 5: shRNA-a and shRNA-b potentiate $H_2O_2$ toxicity and this potentiation is reversed by cotransfection of SOD1a and SOD1b respectively. Cells were transfected and treated with $H_2O_2$. Viability of the cells was measured using an MTS assay (FIG. 5A). Western blot confirmed that the levels of SOD1 correlate with the sensitivity of the cells to $H_2O_2$ (FIG. 5B).

Because SOD1 was known to alleviate $H_2O_2$-induced cellular toxicity (Lee et al. 2001), we tested whether shRNAs would increase the cellular sensitivity to $H_2O_2$ and whether this increase would be reversed by co-expression of the shRNA-resistant SOD1 genes (FIG. 5A). $H_2O_2$ treatment in cells transfected with a non-specific shRNA ("shRNAnsp"; FIG. 5A, bar #2) reduced cell viability by ~25% compared with the untreated cells (FIG. 5A, bar, #1). $H_2O_2$ treatment in cells transfected with either shRNA-a or shRNA-b further reduced the viability to ~50% (FIG. 5A, Bars #3 and #7), indicating that these shRNAs increased the sensitivity of these cells to $H_2O_2$. Wild type SOD1 did not significantly reverse the increased $H_2O_2$ sensitivity that was caused by the expression of either shRNA-a or shRNA-b (FIG. 5, Bars #4 and #8). In contrast, SOD1a reversed the increased $H_2O_2$ sensitivity that was caused by the expression of shRNA-a, but did not reverse the increased sensitivity that was caused by the expression of shRNA-b (FIG. 5. bars, #5 and #6). Conversely, SOD1 b reversed the increased $H_2O_2$ sensitivity that was caused by the expression of shRNA-b, but did not reverse the increased sensitivity that was caused by the expression of shRNA-a (FIG. 5, bars #9, #10). These results correlate with the inhibition of SOD1 expression by the two shRNAs and the resistance to the two shRNAs by their respective replacement genes as shown by Western blotting (FIG. 5B). Thus, shRNA-a and shRNA-b can inhibit the SOD1 expression and reduce SOD1 function, which can be replaced by the expression of their respective RNAi-resistant genes, SOD1a and SOD1b.

In summary, we have designed and demonstrated the concept of a general RNAi strategy for treatment of all ALS cases caused by mutations in SOD1 gene. In this strategy, two regions in SOD1 mRNA are targeted by specific shRNAs. These shRNAs can silence the expression of both the mutant as well as the wild type SOD1. To compensate for the lost function of the wild type SOD1, we have designed two replacement SOD1 genes. These genes are resistant to the silencing by each of these two shRNAs, and thus, can be paired with the shRNAs when applied therapeutically. The shRNA-expressing unit and the replacement SOD1 expression cassette are small. The combined size of the expression cassette for shRNA-a and SOD1a or shRNA-b and SOD1b is 2 kb. Therefore, the shRNA and its paired RNAi-resistant SOD1 gene can be placed in a single viral vector, e.g. an AAV or a lentiviral vector. In this way, every cell that is transduced with the shRNA expressing cassette will also be transduced with the shRNA resistant SOD1 gene. Consequently, while the endogenous mutant and wild type SOD1 genes are silenced by the shRNA, the wild type SOD1 function will be compensated by the replacement SOD1 gene.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inhibiting expression of a human SOD1 gain-of-function target mRNA, and providing for expression of a RNAi resistant replacement gene in a cell comprising administering to the cell a nucleic acid agent comprising a first polynucleotide sequence encoding an RNAi agent specific for the human SOD1 gain-of-function target mRNA, and a second polynucleotide sequence encoding a RNAi resistant replacement gene,
   wherein the RNAi agent comprises an antisense strand having sufficient sequence complementarity to the human SOD1 gain-of-function target mRNA to induce cleavage of the target mRNA, and a sense strand complementary to said antisense strand, and
   wherein the RNAi replacement gene comprises a nucleotide sequence encoding human SOD1 and wherein the RNAi replacement gene comprises SEQ ID NO:3 or SEQ ID NO:85,
   whereby expression of the human SOD1 gain-of-function target mRNA is inhibited and expression of the RNAi resistant replacement gene is achieved.

2. A method of inhibiting expression of a human SOD1 gain-of function target mRNA in a cell, comprising administering to the cell a RNAi agent comprising an antisense strand having sufficient sequence complementarity to RNAi the human SOD1 gain-of-function target mRNA to induce cleavage of the target mRNA, and a sense strand complementary to said antisense strand, said cell expressing an RNAi resistant replacement gene, wherein the RNAi replacement gene comprises a nucleotide sequence encoding human SOD1 and wherein the RNAi replacement gene comprises SEQ ID NO:3 or SEQ ID NO:85,
   whereby expression of the human SOD1 gain-of-function target mRNA is inhibited and expression of the RNAi resistant replacement gene is achieved.

3. The method of claim 1 or 2, wherein the RNAi agent is expressed as an shRNA.

4. A method of treating a subject having a disorder correlated with presence of a human SOD1 dominant gain-of-function target mRNA, the method comprising administering to the subject a therapeutically effective amount of a nucleic acid agent comprising a first polynucleotide sequence encoding an RNAi agent specific for the human SOD1 gain-of-function target mRNA, and a second polynucleotide sequence encoding a RNAi resistant replacement gene,
   wherein the RNAi agent comprises an antisense strand having sufficient sequence complementarity to the human SOD1 gain-of-function target mRNA to induce cleavage of the target mRNA, and a sense strand complementary to said antisense strand, and
   wherein the RNAi replacement gene comprises a nucleotide sequence encoding human SOD1 and wherein the RNAi replacement gene comprises SEQ ID NO:3 or SEQ ID NO:85, thereby treating the disease in a subject.

5. The method of claim 4, wherein the subject is human.

6. The method of claim 1 or 2, wherein the sense strand comprises about 22 nucleotides and the antisense strand comprises about 22 nucleotides.

7. The method of claim 4, wherein the subject is a mammal.

8. The method of claim 1 or 4, comprising administering a cassette or vector comprising the nucleic acid agent.

9. The method of claim 8, wherein the cassette or vector further comprises conditional expression sequences.

10. The method of claim 1, 2 or 4, wherein the antisense strand is encoded by a nucleic acid comprising SEQ ID NO:2.

11. The method of claim 3, wherein the antisense strand is encoded by a nucleic acid comprising SEQ ID NO:2.

12. The method of claim 10, wherein the sense strand is encoded by a nucleic acid comprising SEQ ID NO:1.

13. The method of claim 11, wherein the sense strand is encoded by a nucleic acid comprising SEQ ID NO:1.

14. The method of claim 1, 2 or 4, wherein the RNAi replacement gene comprises SEQ ID NO: 87.

* * * * *

SEQUENCE LISTING

<160> NUMBER OF SEQ ID NOS: 89

<210> SEQ ID NO 1
<211> LENGTH: 22
<212> TYPE: DNA
<213> ORGANISM: Homo sapiens

<400> SEQUENCE: 1
ggcaatgtga ctgctgacaa ag                                        22

```
<210> SEQ ID NO 2
<211> LENGTH: 22
<212> TYPE: DNA
<213> ORGANISM: Homo sapiens

<400> SEQUENCE: 2
ctttgtcagc agtcacattg cc                                                22

<210> SEQ ID NO 3
<211> LENGTH: 22
<212> TYPE: DNA
<213> ORGANISM: Homo sapiens

<400> SEQUENCE: 3
ggaaacgtca cggcggataa ag                                                22

<210> SEQ ID NO 4
<211> LENGTH: 22
<212> TYPE: RNA
<213> ORGANISM: Homo sapiens

<400> SEQUENCE: 4
cuuugucagc agucacauug cc                                                22

<210> SEQ ID NO 5
<211> LENGTH: 21
<212> TYPE: DNA
<213> ORGANISM: Homo sapiens

<400> SEQUENCE: 5
gccgatgtgt ctattgaaga t                                                 21

<210> SEQ ID NO 6
<211> LENGTH: 21
<212> TYPE: DNA
<213> ORGANISM: Homo sapiens

<400> SEQUENCE: 6
atcttcaata gacacatcgg c                                                 21

<210> SEQ ID NO 7
<211> LENGTH: 21
<212> TYPE: RNA
<213> ORGANISM: Homo sapiens

<400> SEQUENCE: 7
aucuucaaua gacacaucgg c                                                 21

<210> SEQ ID NO 8
<211> LENGTH: 21
<212> TYPE: DNA
<213> ORGANISM: Homo sapiens

<400> SEQUENCE: 8
gcagacgtca gtatagagga c                                                 21

<210> SEQ ID NO 9
<211> LENGTH: 19
<212> TYPE: DNA
<213> ORGANISM: Homo sapiens

<400> SEQUENCE: 9
tcatcaattt cgagcagaa                                                    19
```

```
<210> SEQ ID NO 10
<211> LENGTH: 19
<212> TYPE: DNA
<213> ORGANISM: Homo sapiens

<400> SEQUENCE: 10
ttcgagcaga aggaaagta                                                  19

<210> SEQ ID NO 11
<211> LENGTH: 19
<212> TYPE: DNA
<213> ORGANISM: Homo sapiens

<400> SEQUENCE: 11
ggaagcatta aaggactga                                                  19

<210> SEQ ID NO 12
<211> LENGTH: 19
<212> TYPE: DNA
<213> ORGANISM: Homo sapiens

<400> SEQUENCE: 12
aagcattaaa ggactgact                                                  19

<210> SEQ ID NO 13
<211> LENGTH: 19
<212> TYPE: DNA
<213> ORGANISM: Homo sapiens

<400> SEQUENCE: 13
gcattaaagg actgactga                                                  19

<210> SEQ ID NO 14
<211> LENGTH: 19
<212> TYPE: DNA
<213> ORGANISM: Homo sapiens

<400> SEQUENCE: 14
actgactgaa ggcctgcat                                                  19

<210> SEQ ID NO 15
<211> LENGTH: 19
<212> TYPE: DNA
<213> ORGANISM: Homo sapiens

<400> SEQUENCE: 15
tcctcacttt aatcctcta                                                  19

<210> SEQ ID NO 16
<211> LENGTH: 19
<212> TYPE: DNA
<213> ORGANISM: Homo sapiens

<400> SEQUENCE: 16
gcaatgtgac tgctgacaa                                                  19

<210> SEQ ID NO 17
<211> LENGTH: 19
<212> TYPE: DNA
<213> ORGANISM: Homo sapiens

<400> SEQUENCE: 17
ccgatgtgtc tattgaaga                                                  19
```

```
<210> SEQ ID NO 18
<211> LENGTH: 19
<212> TYPE: DNA
<213> ORGANISM: Homo sapiens

<400> SEQUENCE: 18
cgatgtgtct attgaagat                                                  19

<210> SEQ ID NO 19
<211> LENGTH: 19
<212> TYPE: DNA
<213> ORGANISM: Homo sapiens

<400> SEQUENCE: 19
tattgaagat tctgtgatc                                                  19

<210> SEQ ID NO 20
<211> LENGTH: 19
<212> TYPE: DNA
<213> ORGANISM: Homo sapiens

<400> SEQUENCE: 20
tggaagtcgt ttggcttgt                                                  19

<210> SEQ ID NO 21
<211> LENGTH: 19
<212> TYPE: DNA
<213> ORGANISM: Homo sapiens

<400> SEQUENCE: 21
ggaagtcgtt tggcttgtg                                                  19

<210> SEQ ID NO 22
<211> LENGTH: 19
<212> TYPE: DNA
<213> ORGANISM: Homo sapiens

<400> SEQUENCE: 22
ttgctttaaa gtacctgta                                                  19

<210> SEQ ID NO 23
<211> LENGTH: 19
<212> TYPE: DNA
<213> ORGANISM: Homo sapiens

<400> SEQUENCE: 23
taaagtacct gtagtgaga                                                  19

<210> SEQ ID NO 24
<211> LENGTH: 19
<212> TYPE: DNA
<213> ORGANISM: Homo sapiens

<400> SEQUENCE: 24
ccagacttaa atcacagat                                                  19

<210> SEQ ID NO 25
<211> LENGTH: 19
<212> TYPE: DNA
<213> ORGANISM: Homo sapiens

<400> SEQUENCE: 25
gcagttatta tgaggctat                                                  19
```

```
<210> SEQ ID NO 26
<211> LENGTH: 19
<212> TYPE: DNA
<213> ORGANISM: Homo sapiens

<400> SEQUENCE: 26
tcattaactt tgaacaaaa                                                   19

<210> SEQ ID NO 27
<211> LENGTH: 19
<212> TYPE: DNA
<213> ORGANISM: Homo sapiens

<400> SEQUENCE: 27
tcataaattt cgagcagaa                                                   19

<210> SEQ ID NO 28
<211> LENGTH: 19
<212> TYPE: DNA
<213> ORGANISM: Homo sapiens

<400> SEQUENCE: 28
tttgaacaaa aagagagca                                                   19

<210> SEQ ID NO 29
<211> LENGTH: 19
<212> TYPE: DNA
<213> ORGANISM: Homo sapiens

<400> SEQUENCE: 29
ggtagtatca agggtctta                                                   19

<210> SEQ ID NO 30
<211> LENGTH: 19
<212> TYPE: DNA
<213> ORGANISM: Homo sapiens

<400> SEQUENCE: 30
ggcagcataa aaggcctca                                                   19

<210> SEQ ID NO 31
<211> LENGTH: 19
<212> TYPE: DNA
<213> ORGANISM: Homo sapiens

<400> SEQUENCE: 31
gggagcatta aagggctaa                                                   19

<210> SEQ ID NO 32
<211> LENGTH: 19
<212> TYPE: DNA
<213> ORGANISM: Homo sapiens

<400> SEQUENCE: 32
aagtatcaag ggtcttacc                                                   19

<210> SEQ ID NO 33
<211> LENGTH: 19
<212> TYPE: DNA
<213> ORGANISM: Homo sapiens

<400> SEQUENCE: 33
aagcataaaa gggctcaca                                                   19
```

```
<210> SEQ ID NO 34
<211> LENGTH: 19
<212> TYPE: DNA
<213> ORGANISM: Homo sapiens

<400> SEQUENCE: 34
aagcattaaa ggcctaacg                                              19

<210> SEQ ID NO 35
<211> LENGTH: 19
<212> TYPE: DNA
<213> ORGANISM: Homo sapiens

<400> SEQUENCE: 35
gcatcaaggg tcttaccga                                              19

<210> SEQ ID NO 36
<211> LENGTH: 19
<212> TYPE: DNA
<213> ORGANISM: Homo sapiens

<400> SEQUENCE: 36
gcataaaagg cctcacaga                                              19

<210> SEQ ID NO 37
<211> LENGTH: 19
<212> TYPE: DNA
<213> ORGANISM: Homo sapiens

<400> SEQUENCE: 37
gcattaaagg gctaacgga                                              19

<210> SEQ ID NO 38
<211> LENGTH: 19
<212> TYPE: DNA
<213> ORGANISM: Homo sapiens

<400> SEQUENCE: 38
acttaccgag ggtcttcac                                              19

<210> SEQ ID NO 39
<211> LENGTH: 19
<212> TYPE: DNA
<213> ORGANISM: Homo sapiens

<400> SEQUENCE: 39
actcacagaa ggactccat                                              19

<210> SEQ ID NO 40
<211> LENGTH: 19
<212> TYPE: DNA
<213> ORGANISM: Homo sapiens

<400> SEQUENCE: 40
actaacggaa gggctacat                                              19

<210> SEQ ID NO 41
<211> LENGTH: 19
<212> TYPE: DNA
<213> ORGANISM: Homo sapiens

<400> SEQUENCE: 41
tccccatttc aaccccctt                                              19
```

```
<210> SEQ ID NO 42
<211> LENGTH: 19
<212> TYPE: DNA
<213> ORGANISM: Homo sapiens

<400> SEQUENCE: 42
tccacacttt aatccactg                                                19

<210> SEQ ID NO 43
<211> LENGTH: 19
<212> TYPE: DNA
<213> ORGANISM: Homo sapiens

<400> SEQUENCE: 43
tccgcacttt aatccgctc                                                19

<210> SEQ ID NO 44
<211> LENGTH: 19
<212> TYPE: DNA
<213> ORGANISM: Homo sapiens

<400> SEQUENCE: 44
gcaacgttac cgccgataa                                                19

<210> SEQ ID NO 45
<211> LENGTH: 19
<212> TYPE: DNA
<213> ORGANISM: Homo sapiens

<400> SEQUENCE: 45
gcaatgtcac agcagacaa                                                19

<210> SEQ ID NO 46
<211> LENGTH: 19
<212> TYPE: DNA
<213> ORGANISM: Homo sapiens

<400> SEQUENCE: 46
gcaatgtaac ggcggacaa                                                19

<210> SEQ ID NO 47
<211> LENGTH: 19
<212> TYPE: DNA
<213> ORGANISM: Homo sapiens

<400> SEQUENCE: 47
ccgacgtttc catcgagga                                                19

<210> SEQ ID NO 48
<211> LENGTH: 19
<212> TYPE: DNA
<213> ORGANISM: Homo sapiens

<400> SEQUENCE: 48
ccgatgtctc aatagaaga                                                19

<210> SEQ ID NO 49
<211> LENGTH: 19
<212> TYPE: DNA
<213> ORGANISM: Homo sapiens

<400> SEQUENCE: 49
ccgatgtatc gattgaaga                                                19
```

-continued

```
<210> SEQ ID NO 50
<211> LENGTH: 19
<212> TYPE: DNA
<213> ORGANISM: Homo sapiens

<400> SEQUENCE: 50
cgacgtttcc atcgaggac                                                19

<210> SEQ ID NO 51
<211> LENGTH: 19
<212> TYPE: DNA
<213> ORGANISM: Homo sapiens

<400> SEQUENCE: 51
cgatgtctca atagaagat                                                19

<210> SEQ ID NO 52
<211> LENGTH: 19
<212> TYPE: DNA
<213> ORGANISM: Homo sapiens

<400> SEQUENCE: 52
cgatgtatcg attgaagat                                                19

<210> SEQ ID NO 53
<211> LENGTH: 19
<212> TYPE: DNA
<213> ORGANISM: Homo sapiens

<400> SEQUENCE: 53
tatcgaggac tccgttatt                                                19

<210> SEQ ID NO 54
<211> LENGTH: 19
<212> TYPE: DNA
<213> ORGANISM: Homo sapiens

<400> SEQUENCE: 54
tatagaagat tcagtcata                                                19

<210> SEQ ID NO 55
<211> LENGTH: 19
<212> TYPE: DNA
<213> ORGANISM: Homo sapiens

<400> SEQUENCE: 55
tattgaagat tcggtaatc                                                19

<210> SEQ ID NO 56
<211> LENGTH: 19
<212> TYPE: DNA
<213> ORGANISM: Homo sapiens

<400> SEQUENCE: 56
tggtagccgc ttaggctgc                                                19

<210> SEQ ID NO 57
<211> LENGTH: 19
<212> TYPE: DNA
<213> ORGANISM: Homo sapiens

<400> SEQUENCE: 57
tggcagtcga ttggcatgt                                                19
```

```
<210> SEQ ID NO 58
<211> LENGTH: 19
<212> TYPE: DNA
<213> ORGANISM: Homo sapiens

<400> SEQUENCE: 58
tgggagtcgg ttggcgtgt                                               19

<210> SEQ ID NO 59
<211> LENGTH: 19
<212> TYPE: DNA
<213> ORGANISM: Homo sapiens

<400> SEQUENCE: 59
ggtagccgct tagcctgcg                                               19

<210> SEQ ID NO 60
<211> LENGTH: 19
<212> TYPE: DNA
<213> ORGANISM: Homo sapiens

<400> SEQUENCE: 60
ggcagtcgat tggcatgtg                                               19

<210> SEQ ID NO 61
<211> LENGTH: 19
<212> TYPE: DNA
<213> ORGANISM: Homo sapiens

<400> SEQUENCE: 61
gggagtcggt tggcgtgtg                                               19

<210> SEQ ID NO 62
<211> LENGTH: 19
<212> TYPE: DNA
<213> ORGANISM: Homo sapiens

<400> SEQUENCE: 62
ttgccttgaa atatctata                                               19

<210> SEQ ID NO 63
<211> LENGTH: 19
<212> TYPE: DNA
<213> ORGANISM: Homo sapiens

<400> SEQUENCE: 63
ttgcattaaa gtacctgta                                               19

<210> SEQ ID NO 64
<211> LENGTH: 19
<212> TYPE: DNA
<213> ORGANISM: Homo sapiens

<400> SEQUENCE: 64
ttgcgttaaa gtacctgta                                               19

<210> SEQ ID NO 65
<211> LENGTH: 19
<212> TYPE: DNA
<213> ORGANISM: Homo sapiens

<400> SEQUENCE: 65
taaaatatct ttaatgaga                                               19
```

<210> SEQ ID NO 66
<211> LENGTH: 19
<212> TYPE: DNA
<213> ORGANISM: Homo sapiens

<400> SEQUENCE: 66
taaagtacct ctagtgaga                                                19

<210> SEQ ID NO 67
<211> LENGTH: 19
<212> TYPE: DNA
<213> ORGANISM: Homo sapiens

<400> SEQUENCE: 67
taaagtacct atagtgaga                                                19

<210> SEQ ID NO 68
<211> LENGTH: 19
<212> TYPE: DNA
<213> ORGANISM: Homo sapiens

<400> SEQUENCE: 68
ccaaacctag attactgac                                                19

<210> SEQ ID NO 69
<211> LENGTH: 19
<212> TYPE: DNA
<213> ORGANISM: Homo sapiens

<400> SEQUENCE: 69
ccagacataa ataaccgat                                                19

<210> SEQ ID NO 70
<211> LENGTH: 19
<212> TYPE: DNA
<213> ORGANISM: Homo sapiens

<400> SEQUENCE: 70
ccagacgtaa atcacggat                                                19

<210> SEQ ID NO 71
<211> LENGTH: 19
<212> TYPE: DNA
<213> ORGANISM: Homo sapiens

<400> SEQUENCE: 71
gctgtcatca tgagacttt                                                19

<210> SEQ ID NO 72
<211> LENGTH: 19
<212> TYPE: DNA
<213> ORGANISM: Homo sapiens

<400> SEQUENCE: 72
gccgtaataa tgaggctct                                                19

<210> SEQ ID NO 73
<211> LENGTH: 19
<212> TYPE: DNA
<213> ORGANISM: Homo sapiens

<400> SEQUENCE: 73
gcggtgatta tgaggctgt                                                19

<210> SEQ ID NO 74
<211> LENGTH: 874
<212> TYPE: DNA
<213> ORGANISM: Homo sapiens

<400> SEQUENCE: 74

```
ctgcagcgtc tggggtttcc gttgcagtcc tcggaaccag gacctcggcg tggcctagcg      60
agttatggcg acgaaggccg tgtgcgtgct gaagggcgac ggcccagtgc agggcatcat     120
caatttcgag cagaaggaaa gtaatggacc agtgaaggtg tggggaagca ttaaaggact     180
gactgaaggc ctgcatggat tccatgttca tgagtttgga gataatacag caggctgtac     240
cagtgcaggt cctcacttta atcctctatc cagaaaacac ggtgggccaa aggatgaaga     300
gaggcatgtt ggagacttgg gcaatgtgac tgctgacaaa gatggtgtgg ccgatgtgtc     360
tattgaagat tctgtgatct cactctcagg agaccattgc atcattggcc gcacactggt     420
ggtccatgaa aaagcagatg acttgggcaa aggtggaaat gaagaaagta caaagacagg     480
aaacgctgga agtcgtttgg cttgtggtgt aattgggatc gcccaataaa cattcccttg     540
gatgtagtct gaggccccct taactcatct ttatcctgct agctgtagaa atgtatcctg     600
ataaacatta aacactgtaa tcttaaaagt gtaattgtgt gacttttca gagttgcttt     660
aaagtacctg tagtgagaaa ctgatttatg atcacttgga agatttgtat agttttataa     720
aactcagtta aaatgtctgt ttcaatgacc tgtattttgc cagacttaaa tcacagatgg     780
gtattaaact tgtcagaatt tctttgtcat tcaagcctgt gaataaaaac cctgtatggc     840
acttattatg aggctattaa aagaatccaa attc                                 874
```

<210> SEQ ID NO 75
<211> LENGTH: 21
<212> TYPE: RNA
<213> ORGANISM: Homo sapiens

<400> SEQUENCE: 75
cuuugucagc agucacauug c         21

<210> SEQ ID NO 76
<211> LENGTH: 21
<212> TYPE: RNA
<213> ORGANISM: Homo sapiens

<400> SEQUENCE: 76
aucuucaaua gacacaucgg c         21

<210> SEQ ID NO 77
<211> LENGTH: 21
<212> TYPE: RNA
<213> ORGANISM: Homo sapiens

<400> SEQUENCE: 77
uuugucagca gucacauugc c         21

<210> SEQ ID NO 78
<211> LENGTH: 20
<212> TYPE: RNA
<213> ORGANISM: Homo sapiens

<400> SEQUENCE: 78
uugucagcag ucacauugcc           20

<210> SEQ ID NO 79
<211> LENGTH: 21

<210> SEQ ID NO 79
<211> LENGTH: 21
<212> TYPE: RNA
<213> ORGANISM: Homo sapiens

<400> SEQUENCE: 79
uucacggguc cauuacuuuc c                                              21

<210> SEQ ID NO 80
<211> LENGTH: 21
<212> TYPE: RNA
<213> ORGANISM: Homo sapiens

<400> SEQUENCE: 80
gaacauggaa uccaugcagg c                                              21

<210> SEQ ID NO 81
<211> LENGTH: 21
<212> TYPE: RNA
<213> ORGANISM: Homo sapiens

<400> SEQUENCE: 81
agucagaccu uuaaugcuuc c                                              21

<210> SEQ ID NO 82
<211> LENGTH: 21
<212> TYPE: RNA
<213> ORGANISM: Homo sapiens

<400> SEQUENCE: 82
uuacaccaca agccaaacga c                                              21

<210> SEQ ID NO 83
<211> LENGTH: 21
<212> TYPE: RNA
<213> ORGANISM: Homo sapiens

<400> SEQUENCE: 83
gcaaugugac ugcugacaaa g                                              21

<210> SEQ ID NO 84
<211> LENGTH: 21
<212> TYPE: RNA
<213> ORGANISM: Homo sapiens

<400> SEQUENCE: 84
gccgaugugu cuauugaaga u                                              21

<210> SEQ ID NO 85
<211> LENGTH: 21
<212> TYPE: RNA
<213> ORGANISM: Homo sapiens

<400> SEQUENCE: 85
gcaacguaac ggcugacaaa g                                              21

<210> SEQ ID NO 86
<211> LENGTH: 21
<212> TYPE: RNA
<213> ORGANISM: Homo sapiens

<400> SEQUENCE: 86
gccgacguga guauugaaga u                                              21

<210> SEQ ID NO 87
<211> LENGTH: 54

```
<212> TYPE: RNA
<213> ORGANISM: Homo sapiens

<400> SEQUENCE: 87
gggcaacgua acggcugaca aagauggugu ggccgaugug ucuauugaag auuc      54

<210> SEQ ID NO 88
<211> LENGTH: 54
<212> TYPE: RNA
<213> ORGANISM: Homo sapiens

<400> SEQUENCE: 88 gggcaauguga cugcugacaa agauggugug gccgaugugu cuauugaaga uuc       54

<210> SEQ ID NO 89
<211> LENGTH: 54
<212> TYPE: RNA
<213> ORGANISM: Homo sapiens

<400> SEQUENCE: 89
gggcaaugug acugcugaca aagauggugu ggccgacgug aguauugaag auuc       54
```